US007732209B2

(12) United States Patent
Bigot et al.

(10) Patent No.: US 7,732,209 B2
(45) Date of Patent: Jun. 8, 2010

(54) HYPERACTIVE, NON-PHOSPHORYLATED, MUTANT TRANSPOSASES OF MARINER MOBILE GENETIC ELEMENTS

(75) Inventors: Yves Bigot, Saint Avertin (FR); Corinne Auge-Gouillou, Veretz (FR); Marie-Hélène Hamelin, La Membrolle/Choisille (FR); Benjamin Brillet, Orvault (FR)

(73) Assignees: Centre National de la Recherche Scientifique (CNRS), Paris (FR); Universite Francois Rabelais de Tours, Tours (FR)

( * ) Notice: Subject to any disclaimer, the term of this patent is extended or adjusted under 35 U.S.C. 154(b) by 991 days.

(21) Appl. No.: 10/543,718

(22) PCT Filed: Jan. 23, 2004

(86) PCT No.: PCT/FR2004/000161
§ 371 (c)(1), (2), (4) Date: May 24, 2006

(87) PCT Pub. No.: WO2004/078981
PCT Pub. Date: Sep. 16, 2004

(65) Prior Publication Data
US 2007/0031967 A1 Feb. 8, 2007

(30) Foreign Application Priority Data
Jan. 28, 2003 (FR) .................................. 03 00905

(51) Int. Cl.
C12N 15/74 (2006.01)
C12N 15/00 (2006.01)
C12N 15/52 (2006.01)
C12N 1/21 (2006.01)
C07H 21/04 (2006.01)

(52) U.S. Cl. ................. 435/473; 435/320.1; 435/252.3; 435/69.1; 435/183; 536/23.2

(58) Field of Classification Search ........................ None
See application file for complete search history.

(56) References Cited

U.S. PATENT DOCUMENTS 6,368,830 B1    4/2002   Lampe et al.

OTHER PUBLICATIONS

Lohe et al., Genetics, 144, 3, 1087-1095.*
Zhang et al., Nucl. Acids. Res. 29, 3566-3575, 2001.*
Auge-Gouillou, C. et al. (2001). *Mol Genet Genomics* 265:51-65.
Auge-Gouillou, C. et al. (2000). *Mol Genet Genomics* 264:506-513.
Ausubel et al. (1994). In *Current Protocols in Molecular Biology*. Janssen, K. Ed., J. Wiley & Sons, Inc., Massachusetts General Hospital, Harvard Medical School.
Craig et al. (2002). *Mobile DNA II*. ASM Press, Washington. USA.
Felsenstein (1993). Philips (Phylogeny Inference Package) version 3.5.c, University of Washington, Seattle.
Guzman et al. (1995). *J. Bacteriol*, 177:4121-4130.
Jacobson and Hartl (1985). *Genetics*, 111:57-65.
Jeong et al. (2002). *PNAS*, 99:1076-1081.
Kastan et al. (2000). *Nat Rev Mol Cell Biol*, 1:179-186.
Kastan et al. (2001). *Acta Oncol*, 40:686-688.
Ketting et al. (1999). *Cell* 99:133-141.
Lampe, DJ et al. (1996). *EMBO J.*, 15:5470-5479.
Lohe and Hartl (1996). *Mol Biol Evol*, 13:549-555.
Martienssen and Colot (2002). *Science*, 293:1070-1075.
Mornon et al. (2002). *Cell Mol Life Sci.*, 59:2144-2154.
Plasterk, R.H.A. et al. (1999). *Trends in genetics*, 15:326-332.
Renault S. et al. (1997). *Virology*, 1:133-144.
Rubin and Spradling (1982). *Science*, 218:348-353.
Sambrook and Russel (2001). In *Molecular Cloning: a laboratory manual*, 3$^{rd}$ Ed. Cold Spring Harbor Laboratory Press, Cold Spring Harbor, NY.
Tabara et al. (1999). *Cell*, 99:123-132.

* cited by examiner

*Primary Examiner*—Nancy Vogel
(74) *Attorney, Agent, or Firm*—Buchanan Ingersoll Rooney PC

(57) ABSTRACT

The invention relates to hyperactive, non-phosphorylated, mutant transposases of mariner mobile genetic elements. The invention also relates to recombinant nucleotide sequences encoding such transposases. The invention further relates to a method of producing said transposases and to the use thereof for in vitro or in vivo transposition.

19 Claims, 11 Drawing Sheets

Figure 2:
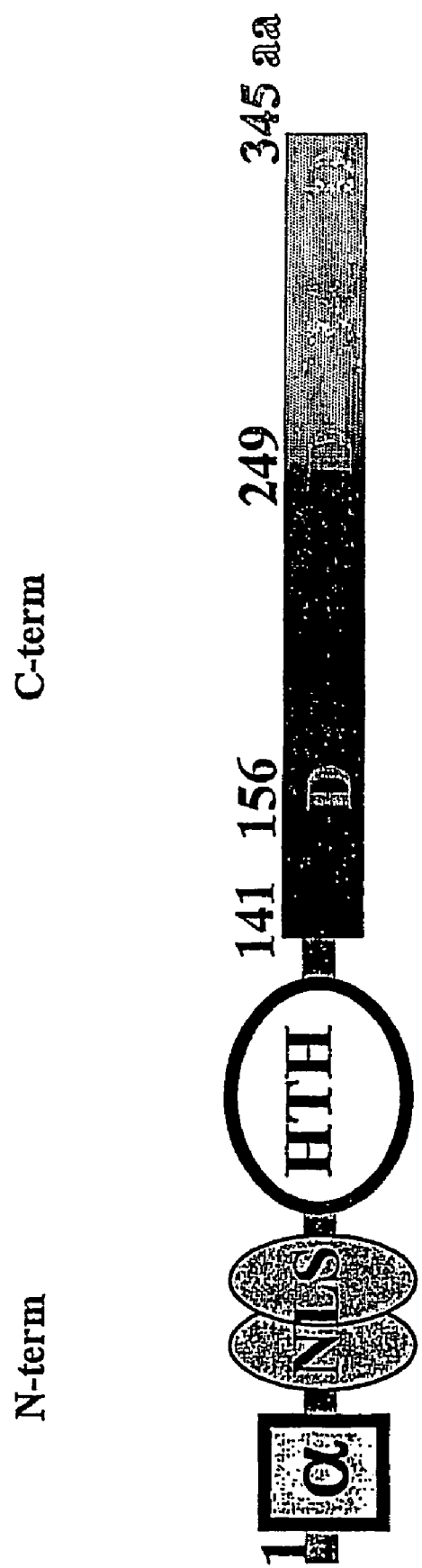

ITR 5' caaggtgtacaagtagggaatgtcggttcgaacatatagatgtctcgcaaacgtaaatatttatcgattgtcataaaactttgaccttgtga 92

```
                                                                        M   S   S    3
agtgtcaaccttgactgtcgaaccaccatagtttggcgcaaattgagcgtcataattgtttactctcagtgcagtcaac ATG TCG AGT 180

F   V   P   N   K   E   Q   T   R   T   V   L   I   F   C   F   H   L   K   K   T   A   A    26
TTC GTG CCG AAT AAA GAG CAA ACG CGG ACA GTA TTA ATT TTC TGT TTT CAT TTG AAG AAA ACA GCT GCG 249

E   S   H   R   M   L   V   E   A   F   G   E   Q   V   P   T   V   K   T   C   E   R   W    49
GAA TCG CAC CGA ATG CTT GTT GAA GCC TTT GGC GAA CAA GTA CCA ACT GTG AAA ACG TGT GAA CGG TGG 318

F   Q   R   F   K   S   G   D   F   D   V   D   D   K   E   H   G   K   P   P   K   R   Y    72
TTT CAA CGC TTC AAA AGT GGT GAT TTT GAC GTC GAC GAC AAA GAG CAC GGA AAA CCG CCA AAA AGG TAC 387

E   D   A   E   L   Q   A   L   L   D   E   D   D   A   Q   T   Q   K   Q   L   A   E   Q    95
GAA GAC GCC GAA CTG CAA GCA TTA TTG GAT GAA GAC GAT GCT CAA ACG CAA AAA CAA CTC GCA GAG CAG 456

L   E   V   S   Q   Q   A   V   S   N   R   L   R   E   M   G   K   I   Q   K   V   G   R    118
TTG GAA GTA AGT CAA CAA GCA GTT TCC AAT CGC TTG CGA GAG ATG GGA AAG ATT CAG AAG GTC GGT AGA 525

W   V   P   H   E   L   N   E   R   Q   M   E   R   R   K   N   T   C   E   I   L   L   S    141
TGG GTG CCA CAT GAG TTG AAC GAG AGG CAG ATG GAG AGG CGC AAA AAC ACA TGC GAA ATT TTG CTT TCA 594

R   Y   K   R   K   S   F   L   H   R   I   V   T   G   D   E   K   W   I   F   F   V   N    164
CGA TAC AAA AGG AAG TCG TTT TTG CAT CGT ATC GTT ACT GGC GAT GAA AAA TGG ATC TTT TTT GTT AAT 663

P   K   R   K   K   S   Y   V   D   P   G   Q   P   S   T   S   T   A   R   P   N   R   F    187
CCT AAA CGT AAA AAG TCA TAC GTT GAT CCT GGA CAA CCG TCC ACA TCG ACT GCT CGA CCG AAT CGC TTT 732

G   K   K   T   M   L   C   V   W   W   D   Q   S   G   V   I   Y   Y   E   L   L   K   P    210
GGC AAG AAG ACG ATG CTC TGT GTT TGG TGG GAT CAG AGC GGT GTC ATT TAC TAT GAG CTC TTG AAA CCC 801

G   E   T   V   N   T   A   R   Y   Q   Q   Q   L   I   N   L   N   R   A   L   Q   R   K    233
GGC GAA ACG GTG AAT ACG GCA CGC TAC CAA CAA CAA TTG ATC AAT TTG AAC CGT GCG CTT CAG AGA AAA 870

R   P   E   Y   Q   K   R   Q   H   R   V   I   F   L   H   D   N   A   P   S   H   T   A    256
CGA CCG GAA TAT CAA AAA AGA CAA CAC AGG GTC ATT TTT CTC CAT GAC AAC GCT CCA TCA CAT ACG GCA 939

S   A   V   R   D   T   L   E   T   L   N   W   E   V   L   P   H   A   A   Y   S   P   D    279
AGA GCG GTT CGC GAC ACG TTG GAA ACA CTC AAT TGG GAA GTG CTT CCG CAT GCG GCT TAC TCA CCA GAC 1008

L   A   P   S   D   Y   H   L   F   A   S   M   G   H   A   L   A   E   Q   R   F   D   S    302
CTG GCC CCA TCC GAT TAC CAC CTA TTC GCT TCG ATG GGA CAC GCA CTC GCT GAG CAG CGC TTC GAT TCT 1077

Y   E   S   V   K   K   W   L   D   E   W   F   A   A   K   D   D   E   F   Y   W   R   G    325
TAC GAA AGT GTG AAA AAA TGG CTC GAT GAA TGG TTC GCC GCA AAA GAC GAT GAG TTC TAC TGG CGT GGA 1146

I   H   K   L   P   E   R   W   E   K   C   V   A   S   D   G   K   Y   F   E               345
ATC CAC AAA TTG CCC GAG AGA TGG GAA AAA TGT GTA GCT AGC GAC GGC AAA TAC TTT GAA taaatgatttt 1217 ttcttttccacaaaatttaacgtgtttttgatttaaaaaaacgacatttcatacttgtacacctga                            1286
```
ITR 3'

FIGURE 1

HYPERACTIVE, NON-PHOSPHORYLATED, MUTANT TRANSPOSASES OF MARINER MOBILE GENETIC ELEMENTS

CROSS REFERENCE TO RELATED APPLICATIONS

This Application is the 35 U.S.C. §371 national stage of International Application No. PCT/FR2004/000161, filed Jan. 23, 2004, which claims priority under 35 U.S.C. §119 of French Application No. 03/00905, filed Jan. 28, 2003.

This invention relates to the field of molecular biology related to transposable elements. The invention is more particularly applicable to an improvement in the properties of natural transposases of mariner mobile genetic elements so that they can be used in biotechnologies.

The purpose of this invention is mutant, non-phosphorylatable, hyperactive transposases of mariner mobile genetic elements.

The invention is also applicable to recombining nucleotidic sequences coding for such transposases.

The invention also relates to a method for production of these transposases and the use of them for in vitro or in vivo transposition.

Transposable elements (TE) or mobile genetic elements (MGE) are small fragments of DNA capable of moving from one chromosomic site to another (Renault et al., 1997). These DNA fragments are characterized by Inverted Terminal Repeats (ITR) located at distal positions 5' and 3'. An enzyme coded by TEs themselves, transposase, catalyses the transposition method for these DNA fragments.

TEs have been identified both in prokaryotes and in eukaryotes (see the book Craig et al., 2002, on this subject).

TEs are distributed into two classes depending on their transposition mechanism. Firstly, class I elements or retrotransposons, transpose via the inverse transcription of an RNA intermediary. Secondly, class II elements transpose directly from one chromosomic site to another via an intermediate DNA using a "cut and paste" type mechanism.

In prokaryotes, a large number of TEs have been listed so far. For example, they include insertion sequences such as IS1, and transposons such as Tn5.

In eukaryotes, class II elements include five families, namely P, PiggyBac, hAT, helitron and Tc1-mariner. mariner-like mobile genetic elements (MLE) form a large group of class II TEs belonging to the Tc1-mariner superfamily (Plasterk et al., 1999).

The capacity of TE transposases to mobilize variable length, homologous or heterologous DNA fragments, including sequences of interest, to insert them in target nucleic acids and particularly in the chromosome of a host, has been and still is broadly used in the biotechnologies field, and particularly in the genetic engineering field.

Among TEs, MLEs have particularly advantageous properties for use in biotechnologies, and particularly in genetic engineering and functional genomics. For example, the following properties can be mentioned non-limitatively:

(i) MLEs are small transposons, easy to manipulate.
(ii) The MLE transposition mechanism is simple. The transposase alone is capable of catalysing all steps involved in the MLE transposition method. Furthermore, it is necessary and sufficient to assure mobility of MLEs in the absence of host factors (Lampe et al., 1996).
(iii) MLEs are characterized in that they are ubiquitous in prokaryotes and eukaryotes. The first MLE, Dmmar1, also called Mos-1 was discovered in *Drosophila mauritiana* by Jacobson and Hartl (1985). Many related elements were subsequently identified in genomes belonging particularly to protozoans, fungi, plants, invertebrates, cold-blooded vertebrates and mammals.
(iv) The transpositional activity of MLEs is highly specific and does not stimulate "resistance" mechanisms of the host genome such as interference phenomena by methylation [MIP; Jeong et al. (2002); Martienssen and Colot (2001)] or via RNA [RNAi; Ketting et al. (1999); Tabara et al. (1999)]. Transposition events may be controlled by various factors such as temperature and pH.

Consequently, there are many potential applications of MLEs in biotechnologies, particularly as genetic recombination tools.

Nevertheless, the transposition efficiency of natural MLEs compared with the efficiency of other TEs, remains low. In particular, MLEs appear to be less active. in eukaryotes than other class II MGEs. In fact, the practical advantage of natural MLEs has been limited so far, since it is important for the manufacturer and for the research worker to have efficient transposases, so as to reduce the number of manipulations and the cost and time necessary to make the required transpositions.

This invention can satisfy these requirements, while benefiting from the advantage of MLE transposases, and overcoming their disadvantages.

This invention demonstrates the fact that MLE transposases are phosphorylated in eukaryotes by means of post-translational modifications (see Experimental Part below). These post-translational modifications have two effects: firstly, they reduce the affinity of transposases for DNA; and secondly, they limit the conformational activation of these enzymes. The end result is a lower capacity of phosphorylated transposases to catalyse transposition in eukaryotes.

Another purpose of the invention is to eliminate one or several phosphorylation sites of these enzymes, by isolated mutagenesis, in order to improve the transpositional properties of MLE transposases.

According to a first aspect, the purpose of this invention is a mutant and hyperactive transposase of MLE.

According to a first embodiment, such a transposase has at least one mutation by conservative substitution of at least one phosphorylatable residue in at least one phosphorylation site, said conservative substitution making said site non phosphorylatable in vivo.

Therefore, a mutant and hyperactive transposase according to the invention is at least partially non-phosphorylatable. In the remainder of this description, such a transposase will be designated as being "mutant, non-phosphorylatable and hyperactive".

For the purposes of this description, a "hyperactive" transposase means a transposase for which the transposition efficiency in eukaryotes is increased by a factor greater than or equal to 10, and preferably greater than or equal to about 25, and even better greater than or equal to about 50, and ideally greater than or equal to about 100.

In particular, a transposase according to the invention is "hyperactive" for at least one function among specific and non-specific DNA binding, dimerisation, transfer of DNA strands, and endonucleasic and nuclear internalisation properties (see FIG. 2 below).

Thus in this context, the expression "hyperactivity of a transposase" means that the biological properties (or functions or activities) of this transposase are improved or increased.

Each of the activities mentioned above is necessary, but may be limiting, during use of the transposition method. In particular, each of these activities can be regulated by post-translation phosphorylations in eukaryotes.

"DNA binding" involves three DNA recognition mechanisms by MLE transposases. The transposases may bind to DNA by their N-terminal domain, either non-specifically (first mechanism) or specifically through ITRs (second mechanism). These two binding modes depend on the conformational state of the N-terminal domain. When the transposases are trapped in the synaptic complex, just after excision of the transposon (this complex comprising at least one dimer of transposases bound to the excised transposon by ITRs), they can bind to the DNA using a third mechanism to recognize the insertion site in the target DNA.

MLE transposases are capable of self-associating ("dimerisation" properties in the context of the invention) using two methods. They can dimerise (homodimers) when they are specifically bound to ITRs. They are also capable of self-oligomerising (homodimers or homooligomers) when they are in an inactive conformation and/or are highly concentrated, when they are not bound to ITRS. In the Mos-1 transposase, the region comprising position T88 (see below) has been suggested as being involved in dimerisation (personal data, Zhang et al., 2001).

The "DNA strand transfer" activity is defined in the literature as covering the capacity of MLE transposases, that are phosphoryl-transferases, to bind DNA fragments at the same time as these fragments are cut.

Therefore, endonucleasic properties are very closely related to the "DNA strand transfer" activity mentioned above. There are three types of cutting activities presented by MLE transposases, namely cutting at the ends of the transposon during excision, linearisation of circular excision intermediaries and cutting of the insertion site in the target DNA.

Finally, MLE transposases have two potential bipartite sites enabling nuclear internalisation.

The terms and expressions "activity", "function", "property", "biological activity", "biological function" and "biological property" are equivalent and have their usual meanings in the technical domain of the. invention. In the context of the invention, the activity concerned is the enzymatic activity of a transposase ("transposase activity" or "transposase function"). Depending on the context, the expression "transposase activity" may generically denote all enzymatic activities of an MLE transposase as mentioned above, or one or several of these activities. In any case, a person skilled in the art will clearly and unambiguously deduce the meaning to be understood by this expression from the context.

According to the invention, a "mutation" denotes. a substitution of one or several bases in a nucleotidic sequence, of one or several amino acids in a proteic sequence. More particularly, for the purposes of this description, a "mutation" should be understood as denoting a substitution of at least one codon base of a nucleotidic sequence coding for an MLE transposase, said substitution leading to the incorporation of a different amino-acid (non phosphorylatable) during translation of the nucleotidic sequence involved, in the position of and replacing the native (phosphorylatable) amino-acid in the resulting proteic sequence.

A mutation by substitution according to the invention must be "conservative", i.e. it must be a non-random solution conserving and preferably improving one or several enzymatic activities of uncontrolled MLE transposases. Preferably, a "conservative" substitution according to the invention improves all enzymatic activities of MLE transposases. This is possible particularly when the global tertiary structure of the MLE transposase is conserved despite the introduced mutation(s) by substitution. A person skilled in the art would know which amino acids substitutions might be appropriate and which substitutions must be avoided (Mornon et al., 2002) so as to conserve the tertiary structure of a protein (in this case a transposase) and improve its biological activity, through his general knowledge.

In particular, a person skilled in the art could refer to Table 1 below that gives a non-limitative list of possible conservative substitutions.

TABLE 1

| Native residue | Conservative substitution |
| --- | --- |
| Ala (A) | Gly; Ser |
| Arg (R) | Lys |
| Asn (N) | Gln; His |
| Cys (C) | Ser; neutral amino-acids |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

In the case of a mutagenesis made on phosphorylation sites, the substitutions may conserve all or some of the activities of the protein, for example if they take place as follows: substitution of a serine or a threonine by a cysteine, an alanine, a valine, a leucine, a tyrosine or an arginine, in order of preference. A conservative substitution appropriate for this context can never be made particularly using a serine, a threonine, an aspartic acid, a glutamic acid or a proline as the substitution residue.

It may be possible to determine other appropriate solutions empirically or from conservative substitutions exemplified in Table 1 above.

In the context of the invention, the "phosphorylation sites" may in particular be phosphorylation sites by the dependent AMPc, GMPc protein kinase, or by the protein kinase C, or by casein kinase II. It may also consist of putative phosphorylation sites, then corresponding to consensus patterns known to a person skilled in the art (PROSITE patterns banks: http://www.infobiogen.fr) as shown in FIG. 1 below. Short sites, not present in PROSITE and corresponding to 4 dipeptides QS, QT, SQ and TQ phosphorylatable by ATM kinases are also taken into account as being "putative phosphorylation sites" (Kastan et al., 2000; Kastan et al., 2001).

Furthermore, phosphorylation sites targeted by the invention may be conserved through at least two MLE transposases. In this case, they may be demonstrated by an alignment of proteic sequences of at least two MLE transposases. For example,. one of these sequences may be the Mos-1 transposase sequence (see the alignment of MLE transposase sequences deposited in the EMBL data bank as access number DS36877). The residues of two distinct proteic sequences thus aligned are called the "corresponding residues" in this description. In order to facilitate the identification of phosphorylatable residues that could be mutated in the sequence of a mariner MGE transposase distinct from sequence SEQ ID No. 2 (sequence of transposase Mos-1), these residues are identified in this invention as being "residues corresponding to the sequence of said mariner MGE transposase aligned with sequence SEQ ID No. 2".

Thus, phosphorylatable residues that could be mutated by conservative substitution are chosen from among:

the following residues in sequence SEQ ID No. 23: T11; T24; S28; T42; T88; S99; S104; T135; S147; T154; S170; T181; S200; T216; T255; and S305, or corresponding residues in the sequence of a mariner MGE transposase aligned with said sequence SEQ ID No. 2, said corresponding residues being chosen from among:

a serine; and a threonine.

According to a second embodiment, a transposase according to the invention will have at least one mutation by conservative substitution of at least one phosphorylatable residue in each phosphorylation site, said conservative substitution making each site non phosphorylatable in vivo.

According to a third embodiment, a transposase according to this invention is such that said phosphorylatable residue used as a target for mutation by conservative substitution is substituted by a non-phosphorylatable residue.

According to a fourth embodiment, a mutant, non-phosphorylatable, hyperactive transposase according to the invention originates from an MLE belonging to the mauritiana subfamily.

"MLEs" targeted in this invention have sequence similarities equal to at least 50% and preferably 75% or even better 80%, and ideally at least 90% between them. Alternately, MLEs according to the invention have sequence similarities of at least 80%, preferably at least 90%, even better at least 95% and ideally at least 98%. Thus, the MLEs in question have at least 50%, preferably at least 75%, even better at least 80% and ideally at least 90% of identical bases along the entire length. Alternately, the MLEs have at least 80%, preferably at least 90%, even better at least 95% or ideally at least 98% of identical bases along their entire length. The identical bases may be consecutive, entirely or only partly. The MLEs thus envisaged may have the same length or a different length if their sequences include deletions or insertions of one or several bases.

The "mauritiana subfamily" contains MLEs for which the transposases are coded by sequences that are sufficiently similar over their entire length or in regions coding for the N- and C-terminal ranges only, in other words at least 75%, so that they can be included in the same alignment as the four sequences below, during phylogenetic studies carried out using parsimony and "Neighbour-Joining" methods on a set of data consisting of 1000 subsamples (1000 "bootstrap" subsamples) [See Felsenstein (1993) and Augé-Gouillou et al. (2000)]:

Mos-1 transposase (SEQ ID No. 2, EMBL access No. X78906);

Mayetiola destructor Mdmar-1 transposase (EMBL access No. U24436);

Bombus terrestris Btmar-1 transposase (sequence No. 3 in the alignment of EMBL access No. DS36877), and Metaseuilius occidentalis Momar-1 transposase (EMBL access No. U12279).

According to a fifth embodiment, a mutant, non-phosphorylatable, hyperactive transposase according to the invention originates from the Mos-1 MLE.

In particular, in one mutant, non phosphorylatable, hyperactive transposase originating from the mos-1 MLE, one or several phosphorylatable residues among the following residues (with reference to sequence SEQ ID No. 2): T11; T24; S28; T42; T88; S99; S104; T135; S147; T154; S170; T181; S200; T216; T255 and S305, are substituted by non phosphorylatable residues.

Advantageously, at least the T88 phosphorylatable residue or alternately at least the S104 phosphorylatable residue of such a transposase is substituted by a non-phosphorylatable residue. In particular, at least the T88 and S104 residues are substituted by non-phosphorylatable residues.

According to a second aspect, this invention relates to a recombining nucleotidic sequence coding for a transposase like that described above.

A "nucleotidic sequence" or a "nucleic acid" according to the invention are conforming with the usual acceptance in the biological field. These two expressions indifferently cover DNAs and RNAs, the DNA possibly being genomic, plasmidic, recombining, complementary (cDNA) and the RNA possibly being messenger RNA (mRNA), ribosomal RNA (rRNA) or transfer RNA (tRNA). Preferably, nucleotidic sequences and nucleic acids in the invention are DNAs.

According to a third aspect, this invention relates to a recombining vector comprising at least one recombining nucleotidic sequence coding for a transposase according to the invention.

Advantageously, such a recombining vector can be used to express said recombining nucleotidic sequence.

According to a fourth aspect, the purpose of this invention is a recombining host cell harboring at least one recombining vector like that described above.

Since MLEs do not at the moment have any host restriction, a recombining host cell according to the invention may have a eukaryote or prokaryote origin.

For example, and non-limitatively, it could be a eukaryotic cell originating from a yeast, a fungus, a plant, an insect (e.g. *drosophila*), a rodent or a mammal (e.g. rabbit).

Alternately, a cell suitable for use of the invention may originate from bacteria (e.g. *Escherichia coli*).

According to a fifth aspect, this invention relates to a method for production of a mutant, non-phosphorylatable, hyperactive transposase like that described above.

According to a first embodiment, a method conforming with the invention comprises at least:

a) cloning of the recombining nucleotidic sequence coding for the mutant, non-phosphorylatable, hyperactive transposase in an expression vector;

b) transformation of a host cell with. said recombining expression vector; and c) expression of said nucleotidic sequence by said recombining host cell.

All steps used in the context of such a method make use of conventional techniques known to the persons skilled in the art (for example see Sambrook and Russel, 2001).

In particular, the term "transformation" in this case has a generic meaning in that, apart from the transformation in the strict sense of the term, it also includes transduction by a viral vector and transfection, all routine molecular biology techniques for a person skilled in the art.

According to a second embodiment, such a method also includes a prior step to obtain the said recombining nucleotidic sequence by substitution of at least one nucleotide of a triplet or codon coding for a phosphorylatable residue by another nucleotide, in the nucleotidic sequence coding for the corresponding native transposase, so that the resulting triplet codes for a non-phosphorylatable residue. This preliminary step is derived from site-directed mutagenesis techniques known to a person skilled in the art (Ausubel et al., 1994).

According to a third embodiment of the method according to the invention, a subsequent step is carried out to purify said transposase.

Preferably, according to this invention, the purification step mentioned above consists of using conventional methods known to a person skilled in the art, to purify the proteic fraction possessing the required enzymatic activity, and not the enzyme itself. This active proteic fraction thus purified is referred to in this description as a "pure enzyme" or "pure transposase". According to this definition, at the end of this step, the presence of minority quantities of contaminating substances including other proteins may be acceptable, provided that the activity of the transposase of interest is conserved, and that only this activity is detected. The enzymatic activity of interest can be detected using conventional methods known to a person skilled in the art (Ausubel et al., 1994).

During implementation of a method like that described above, the host cell is chosen from among prokaryotic cells, for example bacteria, and eukaryotic cells, for example yeast, fungi, plants, insects and mammals.

According to a sixth aspect, this invention relates to uses of at least one mutant, non-phosphorylatable, hyperactive transposase as described above, in the biotechnologies field.

According to a first embodiment, such a transposase is used for the in vitro transposition of a transposable DNA sequence of interest to a target DNA sequence.

According to a second embodiment, the method according to the invention is used for in vivo transposition of a transposable DNA sequence of interest into the host genome.

Alternately, a transposase according to the invention might be useful to prepare a medicament for in vivo transposition of a sequence of transposable DNA of interest into the host genome.

The use of in vitro or in vivo transposition depends on the general knowledge of persons skilled in the art in the field of the invention (Ausubel et al., 1994; Craig et al., 2002).

In this description, a "host" should be understood as being an organism, eukaryote or prokaryote, or a tissue of an organism, or a cell of an organism or a tissue.

The following figures are given for guidance only and in no way limit the subject of this invention.

FIG. 1: Nucleotidic sequence of mos-1 transposon (SEQ ID No. 1) and proteic sequence of the Mos-1 transposase (SEQ ID No. 2). The putative phosphorylation sites are located as follows:

simple box: putative phosphorylation site by the AMPc, GMPc-dependent protein kinase;

box in dashed line: putative phosphorylation site by protein kinase C;

double box: putative phosphorylation site by casein kinase II.

Residues shown in light text in the sequence (QTQ; positions 87 to 89 in the proteic sequence SEQ ID No. 2) correspond to the site of putative phosphorylation by the ATM kinases family.

Residues surrounded by circles are Asp residues involved in the catalytic triad characteristic of MLE transposases (D, D34-35[D/E]).

FIG. 2: Scheme representing the structure of the transposase of the Mos-1 element.

N-term: N-terminal domain responsible for binding to ITRs;

C-term: C-terminal domain responsible for catalysis of the transfer of DNA stands; NLS=putative nuclear localizing (or nuclear internationalisation) signal; HTH=helix-turn-helix pattern; aa=amino acid.

The numbers indicate the positions of amino acids.

The characteristic catalytic triad [D, D34(D/E)] is signalled.

Figure 3:
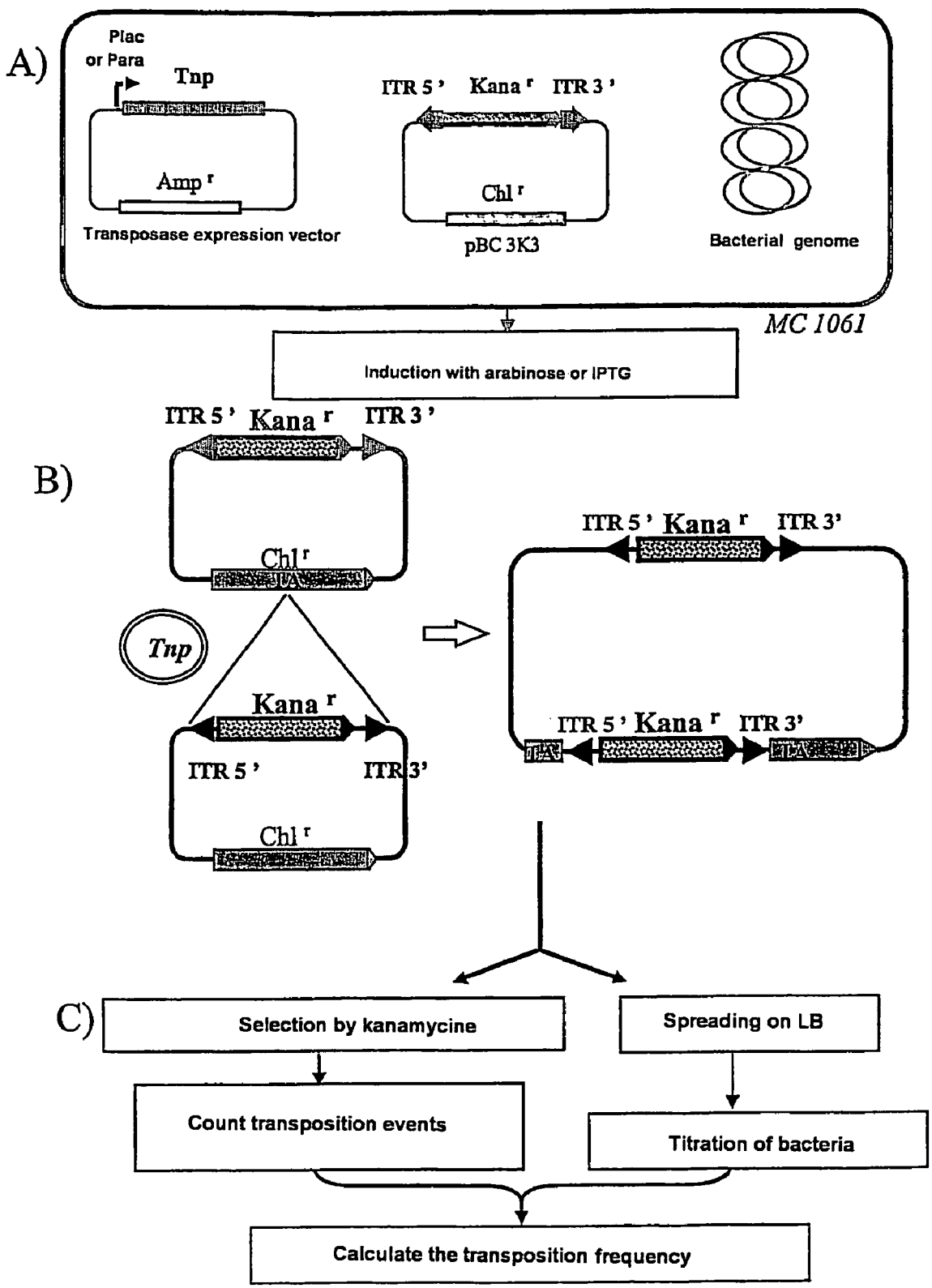

FIG. 3: Diagrammatic view of the transposition test.

A): co-transformed bacteria with the expression vector coding for transposase (Tnp) and the transposition reporter vector.

B): Transposition event after induction of the expression vector.

C): Determination of the transposition frequency.

Figure 4:
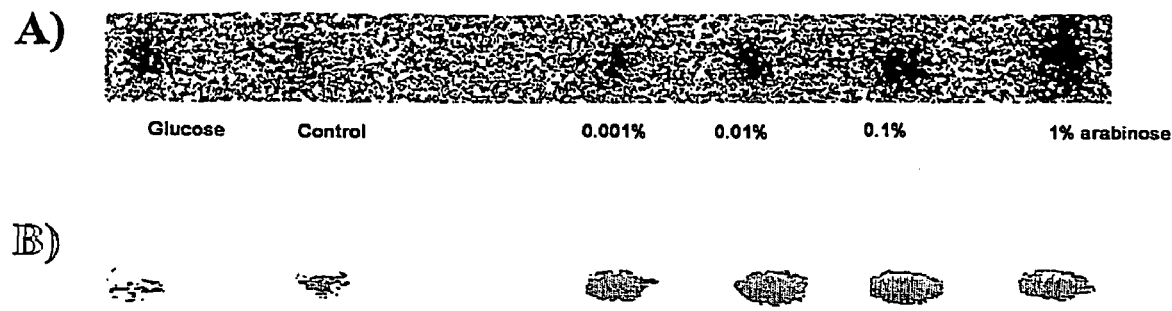

FIG. 4: pBadR-Tnp mRNA "dots" hybridised with:
the L27 probe (A); and
the Tnp probe (B).

Figure 5:
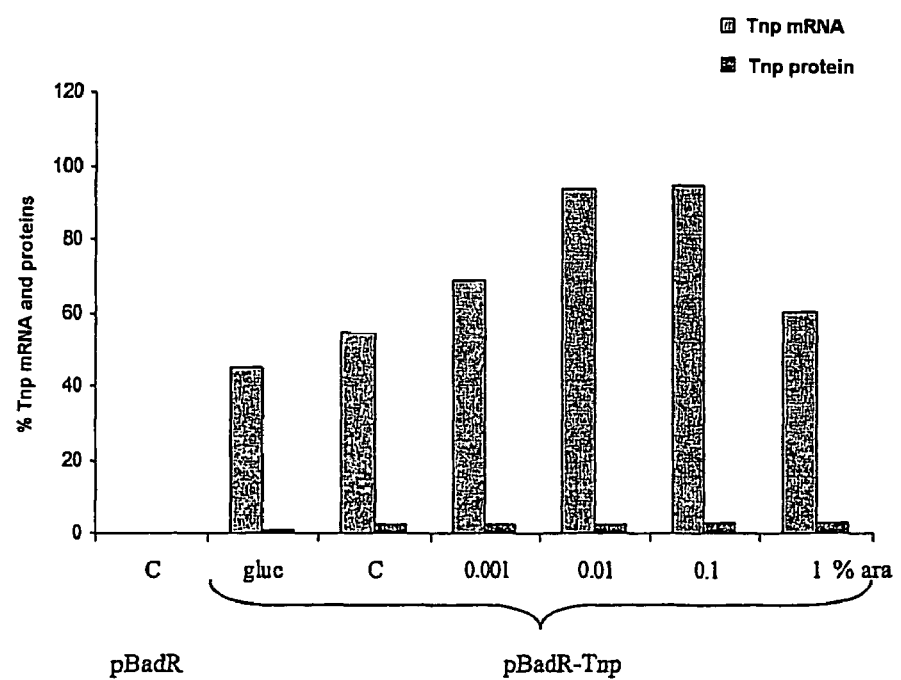

FIG. 5: Graph showing the Tnp mRNA/Transposase correlation as a function of culture conditions in the pBadR expression system.

Figure 6:
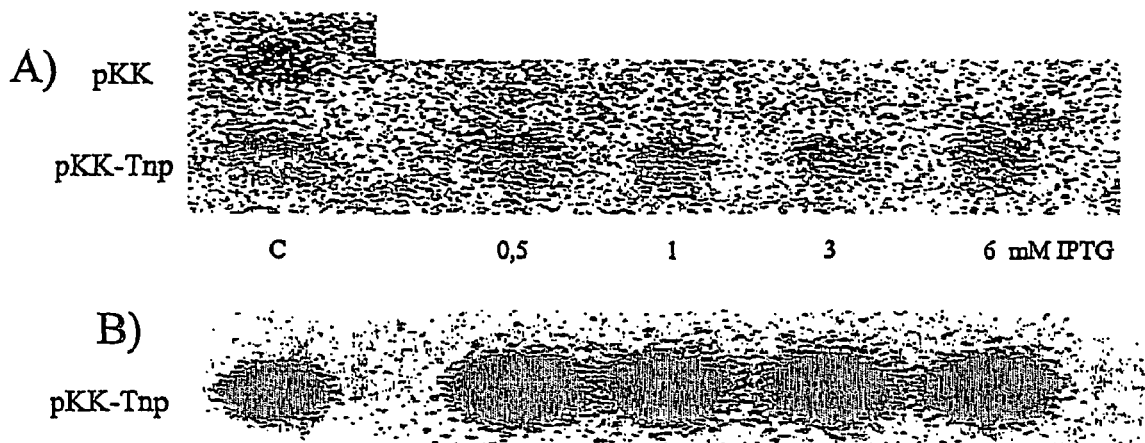

FIG. 6: pKK-Tnp mRNA "dots" hybridised with:
the L27 probe (A); and
the Tnp probe (B).

Figure 7:
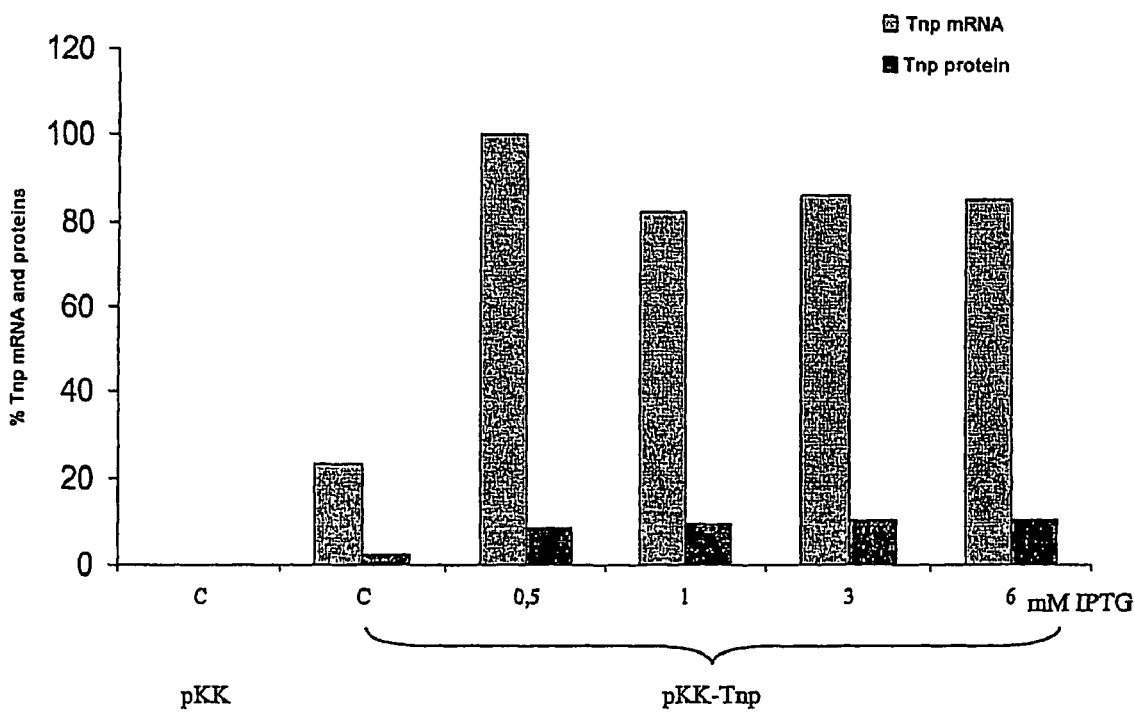

FIG. 7: Graph showing the Tnp mRNA/Transposase correlation as a function of culture conditions in the pKK expression system.

Figure 8:
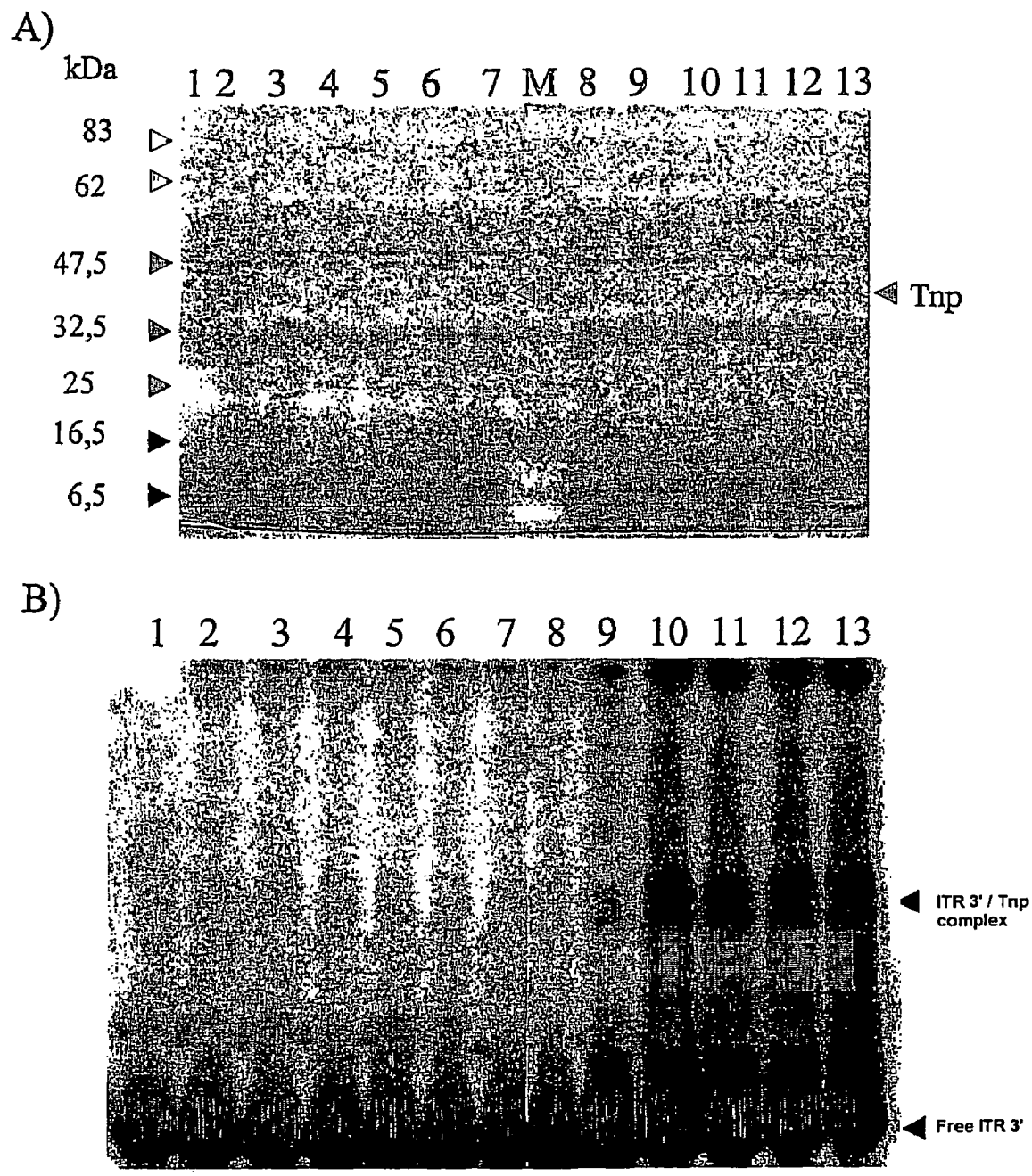

FIG. 8: Photograph of a 10% SDS-PAGE protein gel of proteic extracts (A) and autoradiogram of delay on gel of transposases in the presence of ITR 3' (B).

Lane 1=pBadR control

Lanes 2 to 7=Tnp output from the pBadR-Tnp system (2=1% glucose, 3=control, 4=0.001% ara, 5=0.01% ara, 6=0.1% ara, 7=1% ara)

Lane 8: pKK control

Lanes 9 to 13: Tnp output from the pKK-Tnp system (9=control, 10=0.5 mM IPTG, 11=1 mM IPTG, 12=3 mM IPTG; 13=6 mM IPTG)

M: precoloured size marker (P7708S, New England BioLabs)

Figure 9:
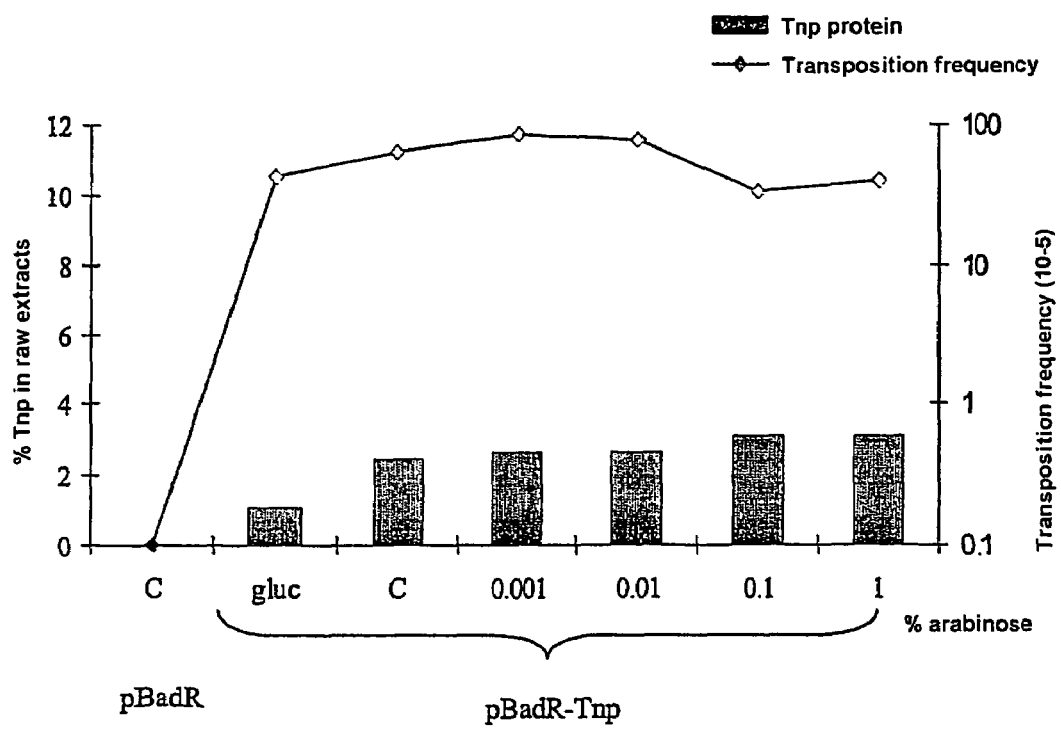

FIG. 9: Graph showing the transposition frequency and enrichment in transposase as a function of culture conditions in the pBadR expression system.

Figure 10:
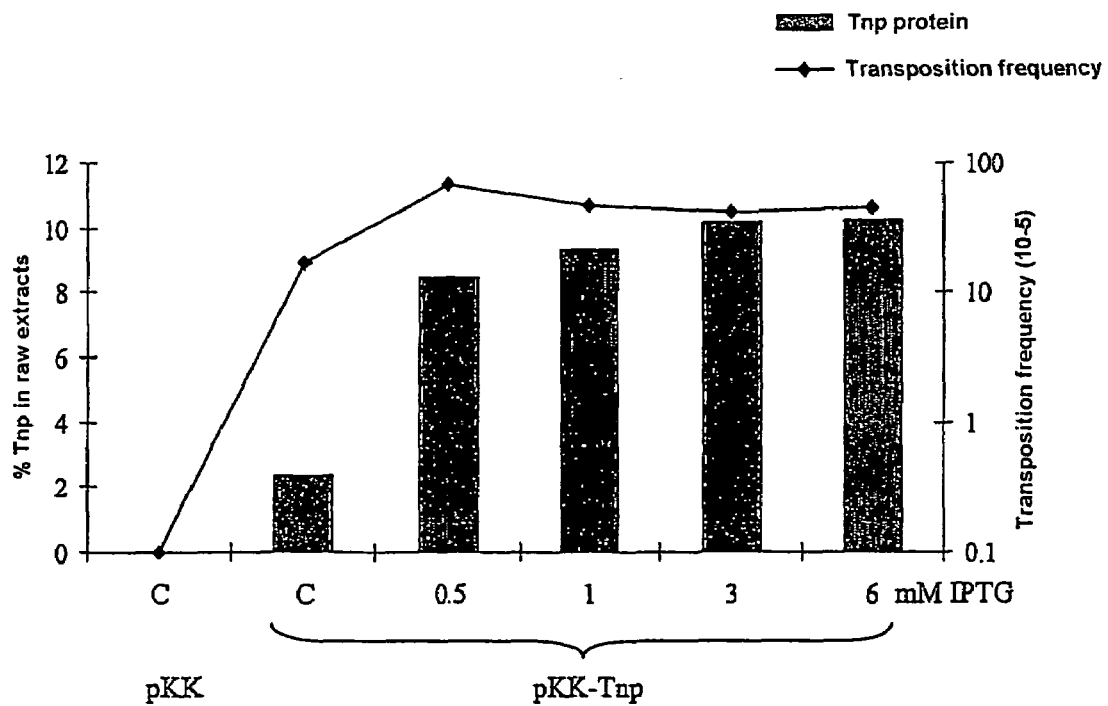

FIG. 10: Graph showing the transposition frequency and enrichment in transposase as a function of culture conditions in the pKK expression system.

Figure 11:
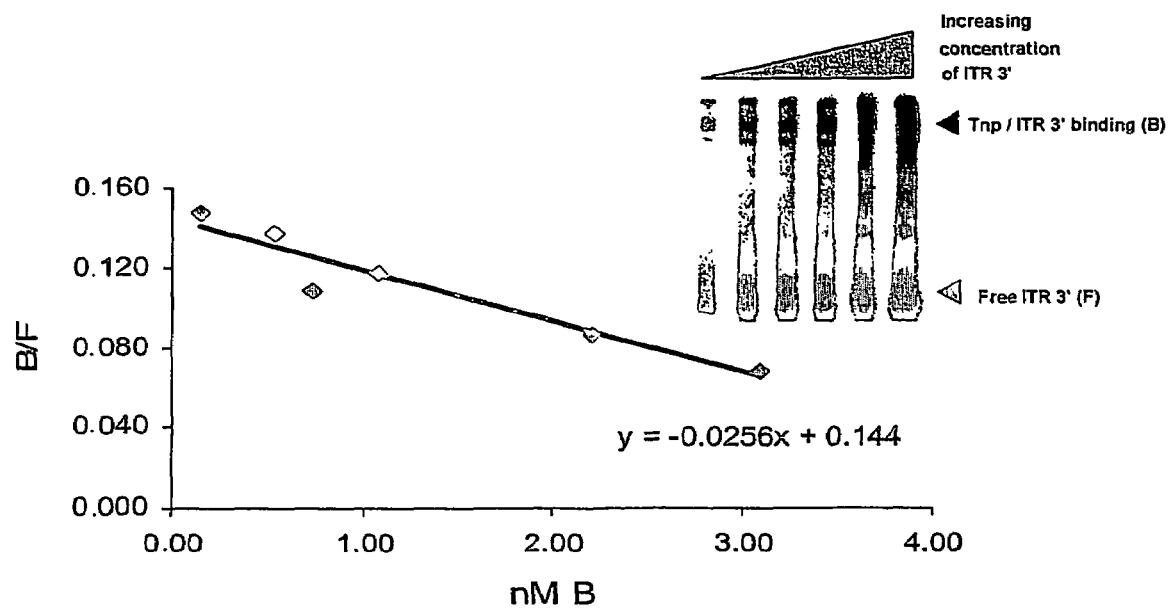

FIG. 11: Scatchard plot of binding to ITR saturation experiments, with MBP-Tnp produced in insect cells.

Figure 12:
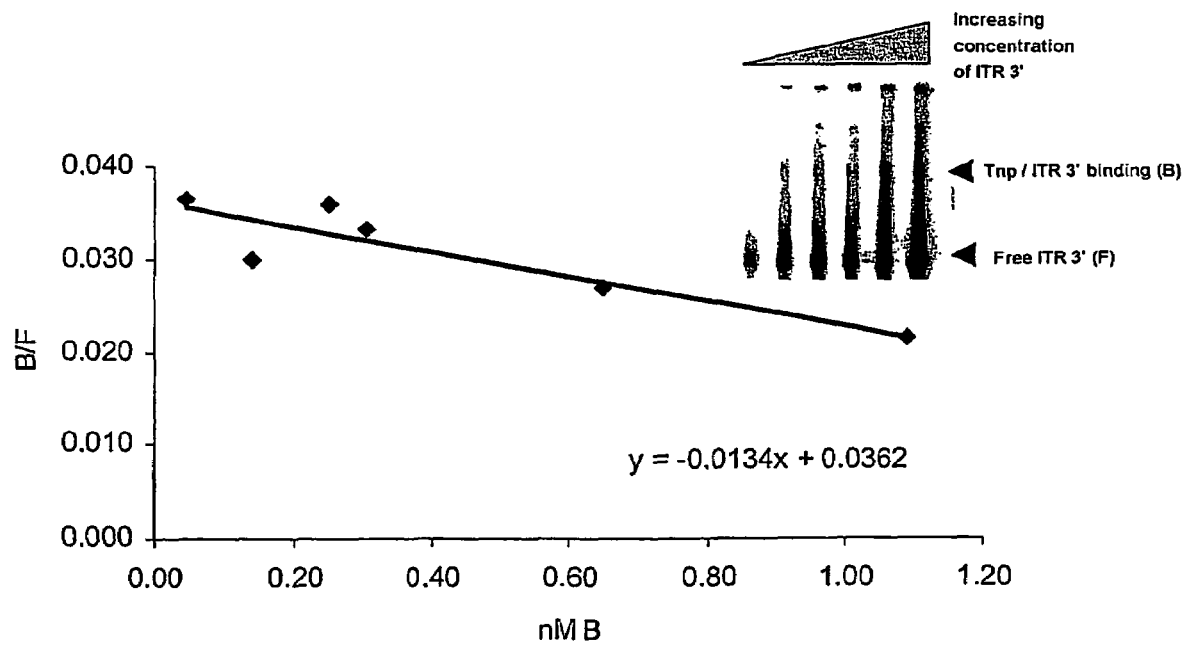

FIG. 12: Scatchard plot of binding to ITR saturation experiments with eukaryotic Tnp produced in vitro.

Figure 13:
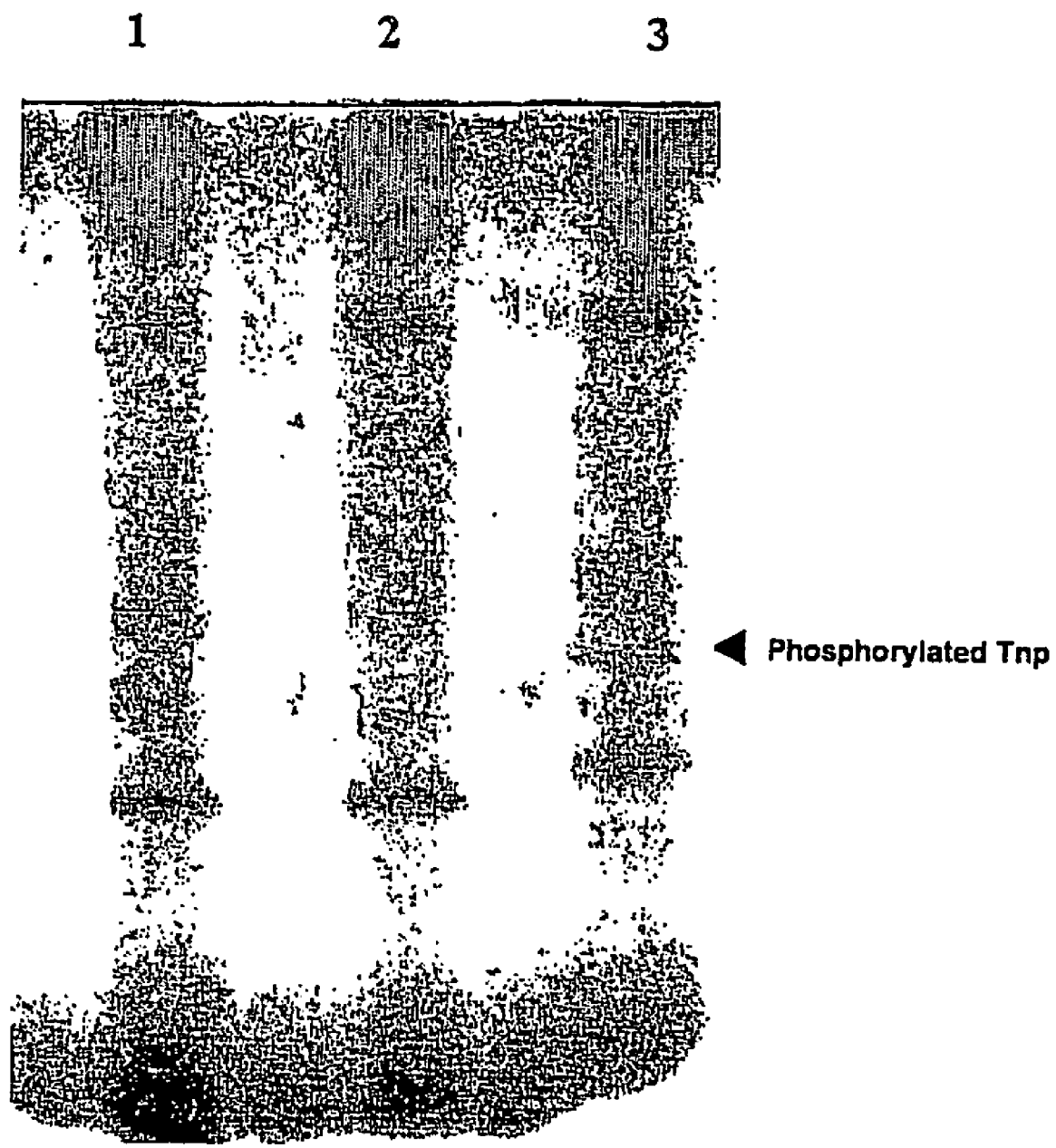

FIG. 13: Autoradiogram of an SDS-Page 10% acrylamide gel of different in vitro syntheses in the presence of ATP-$\gamma^{32}$P.

1: without DNA

2: with the pET-26b+vector

3: with the pET-Tnp vector (300 ng)

Figure 14:
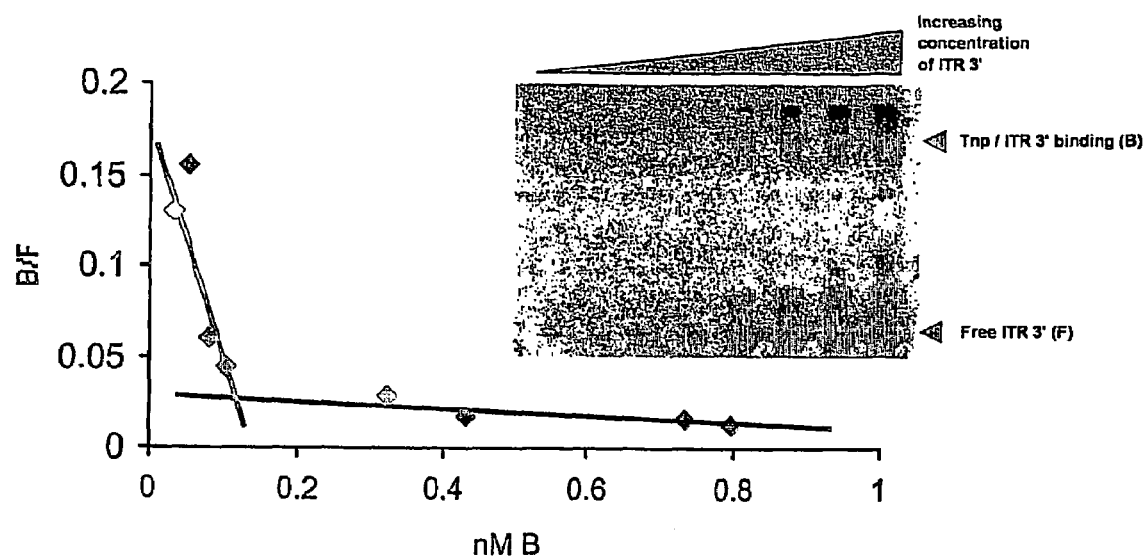

FIG. 14: Scatchard plot of binding to ITR saturation experiments with dephosphorylated MBP-Tnp.

Figure 15:
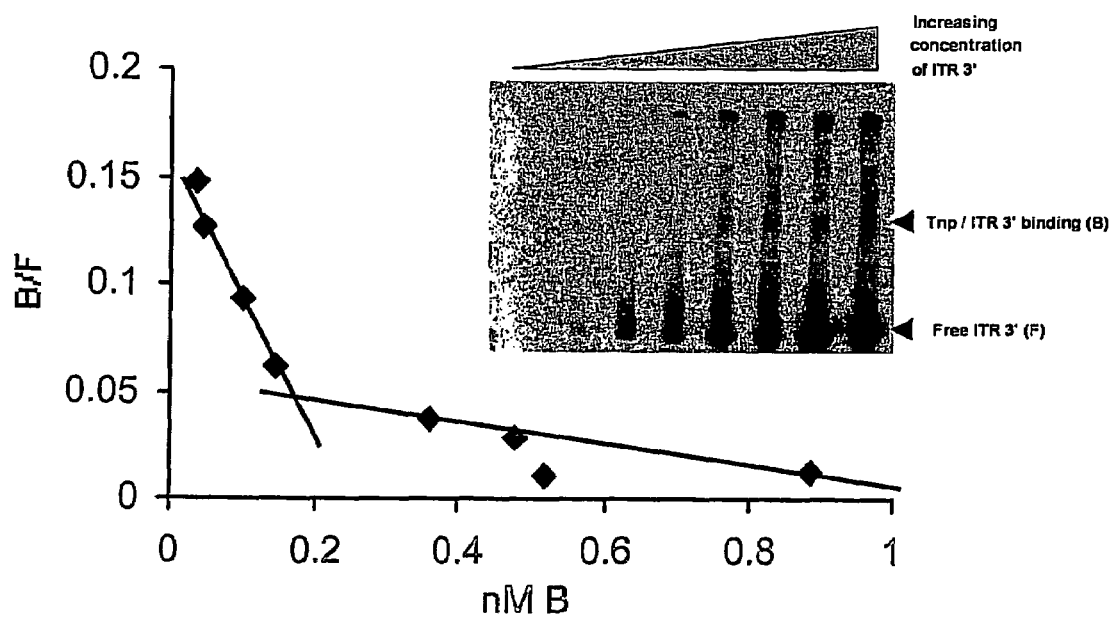

FIG. 15: Scatchard plot of binding to ITR saturation experiments with dephosphorylated Tnp produced in vitro.

Figure 16:
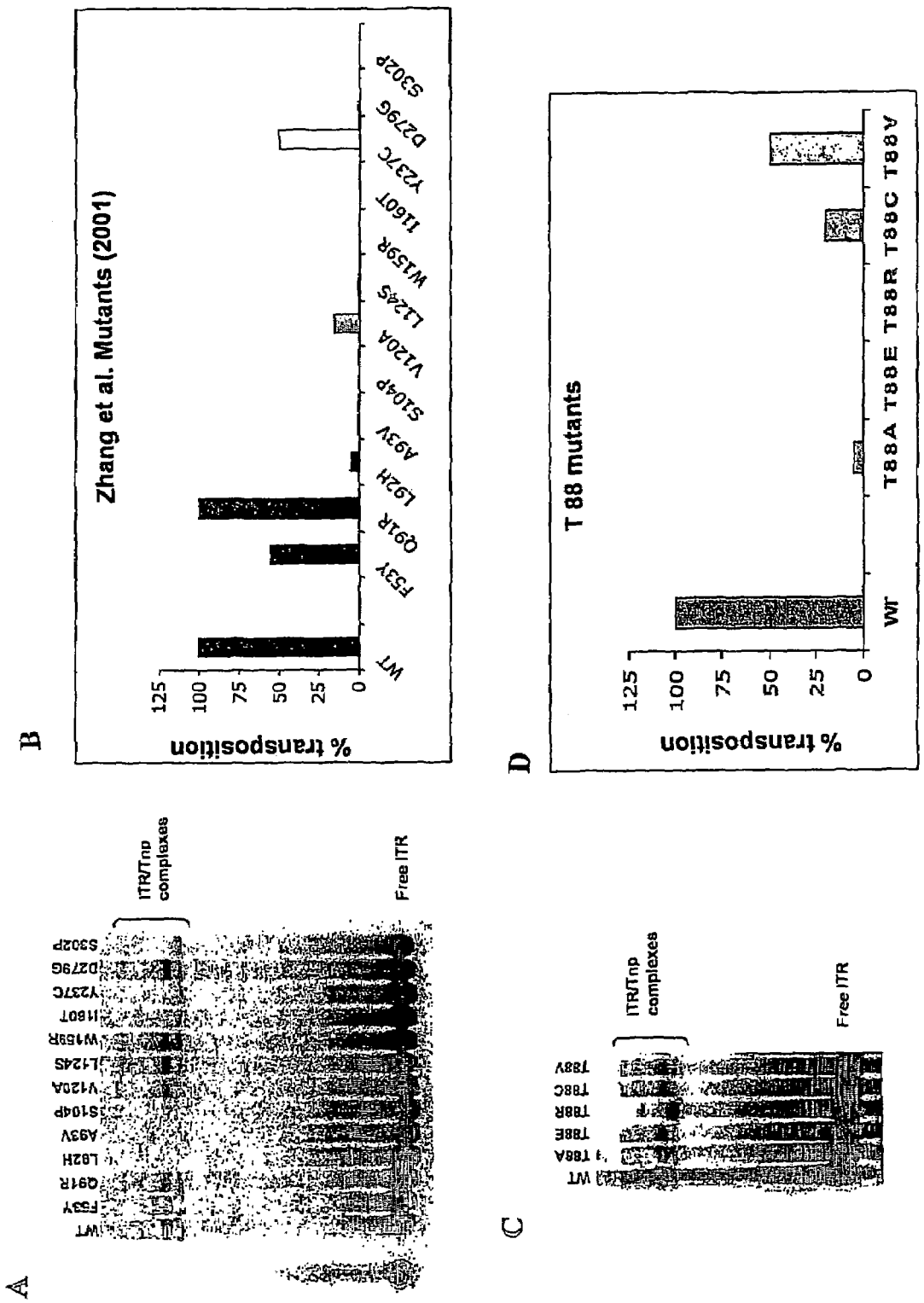

FIG. 16: Autoradiograms and graphs illustrating delay on gel analysis results (A and C) and transposition in bacteria results (B and D) obtained by Zhang et al. transposases (2001) (A and B) and transposases mutated on position T88 (C and D).

WT: wild transposase.

The experimental part described below is based on examples and figures, and provides a non-limitative illustration of the invention.

1. Material and Methods

1.1. Description of Vectors Used

The pBadR-Tnp vector (5.6 kb) enables the expression of transposase under the control of a weak, modulable promoter inducible with arabinose (Para) and repressed in the presence of glucose by means of the AraC protein (coded by this vector). PBadR-Tnp carries an ampicilline resistance gene. Its construction is given in detail in section 1.2.1 below.

The pKK-Tnp vector (5.6 kb) enables a strong expression of transposase through a Plac promoter inducible with IPTG. The promoter is not modulable and has a leak with a natural expression. PKK-Tnp also carries an ampicilline resistance gene. Construction of the vector is shown in section 1.1.2. below.

pBC 3K3 is a plasmide donor of pseudo mariner Mos-1 (Augé-Gouillou et al. 2001). It contains the "OFF" kanamycine resistance gene (in other words without the promoter) bordered by two ITRs 3'. Thus, only bacteria that will have made the transposition of the pseudotransposon on the output side of a promoter ("tagging" promoter) will be selected on LBkanamycine boxes. The vector carries a chloramphenicol resistance gene.

The pBS (3') carries the ITR 3' cloned on the SmaI site of pBS (Stratagene, La Jolla, Calif., United State). The pBS is identical to the pBC, except that it carries an ampicilline resistance gene instead of a chloramphenicol resistance gene.

The pET-Tnp vector (6.4 kb) (Augé-Gouillou et al., 2001) codes for transposase under the control of the T7 promoter and has a kanamycine resistance gene. This vector was used as a source of DNA for in vitro transcription/translation of reticulocytes in lysate to produce a eukaryotic transposase. BL21 bacteria, coding for the polymerase T7 under the control of the Plac inducible with IPTG, were transformed with pET-Tnp to produce prokaryote transposase in the phosphorylation test described below.

The pGEM®-T-Easy vector (Promega, Charbonnières, France) has Pu and pRev sequencing primers (Ausubel et al., 1994) and the ampicilline resistance gene. It is designed to clone PCR products in the LacZ gene, which enables white/blue screening of bacterial colonies obtained on the LBampicilline box in the presence of IPTG and X-Gal. It was used to give pGEM-T (Tnp) (Augé-Gouillou et al., 2001) and the pGEM-T (L27) for which the construction is described in detail in section 1.2.3. below.

1.2. Construction of Vectors

1.2.1. Preparation of Vector DNA

For the different constructions, all the DNA elutions starting from an aragose gel were made using the Geneclean II kit (BIO 101, UK). All minipreparations of plasmides from a bacterial culture were made using the Minipreps Plus Wizard kit (Promega).

1.2.2. pBadR-Tnp

The pBadR-Tnp was obtained from pBad 18 in two steps:
Cloning of RBS (Ribosome Binding Site)
Cloning of an RBS in pBad 18 reconstitutes the following sequence:

```
5' GAAGGAGTAcccgggGATC 3'    (SEQ ID No. 3)
```

This sequence corresponds to a translation initiation consensus site if the gene coding for the transposase is cloned in a SmaI site (in lower case letters). The RBS was purchased in the form of two single strand complementary non-phosphorylated oligonucleotides. Matching of the two strands reconstitutes the following sequence:

```
5'AATTC GATATCGAAGGAGTAC 3'    (SEQ ID No. 4)
3'G CTATAGCTTCCT 5'.           (SEQ ID No. 5)
```

The output end 5' corresponds to an EcoRI site, the output end 3' corresponds to a KpnI site used to clone RBS in pBad18. This sequence also provides a unique EcoRV site (in italics) that can be used to control cloning.

The two matched strands were phosphorylated with T4 polynucleotide kinase (New England BioLabs, Beverly, Mass. United States). The pBad plasmide 18 was digested by KpnI and EcoRI and then dephosphorylated. The RBS (15 ng) was then ligated with plasmide (25 ng) overnight at 16° C. in the presence of a T4 DNA ligase (Promega) to obtain the pBadR. Competent bacteria E. coli MC1061 (strain with no active transport of arabinose) were transformed with pBADR on the LB box (5 g of NaCl, 5 g of yeast extract, 10 g of tryptone, 0.3 ml of 10N NaOH, H2O to make 1 liter)/ampicilline (100 µg/ml). Twelve ampicilline resistance colonies were put into culture to extract plasmidic DNA and analyse the plasmide by EcoRV digestion. The plasmidic DNAs were sequenced using "the DNA sequencing kit" by Perkin Elmer Biosystems (Courtaboeuf, France) and analysed on a Licor type monolaser automatic sequencer (Science Tec, Parc d'Innovations des Ulysses, France) in order to check which plasmides had integrated a single RBS. The plasmide containing a single RBS was then used to clone the gene coding for transposase.

Cloning the Gene Coding for Transposase:

The fragment coding for transposase (Tnp) was prepared from the pGEM-T (Tnp) vector by SnaBI/HindIII digestion and eluted on a 0.8% agarose gel (TAE 1×: 0.04 M Tris-acetate, 1 mM EDTA, pH 8). The pBadR plasmide obtained previously was digested by SmaI/HindIII. After electrophoresis on an agarose gel, the plasmide DNA was eluted and then ligated with the fragment coding for Mos-1 transposase (referred to as Tnp in this experimental part), at 25 ng of fragment for 25 ng of vector. The ligation product was used to transform E. Coli MC1061 bacteria which were then selected on the LB-ampicilline box (100 µg/ml). 12 ampicilline resistance clones were put into culture for an extraction of plasmide. The DNA mini-preparations were checked by EcoRV/Hind/III digestion then in an electrophoresis on 0.8% agarose gel (TAE 1×) to assure that they had included the gene coding for transposase.

1.2.3. pKK-Tnp:

The fragment coding for mariner Mos-1 transposase (Tnp) was prepared from PGEM-T (Tnp) by NcoI/HindIII digestion and was eluted on gel. It was ligatured with the pKK-233-2 vector (Clontech, Ozyne, Saint-Quentin-en-Yvelines, France), opened by the same enzymes at a content of 10 ng of vector for 40 ng of Tnp fragment, to give pKK-Tnp. MC1061 bacteria were transformed with the pKK-Tnp expression vector, spread on an LB-ampicilline box (100 µg/ml), 50 mM of CaCl$_2$ and placed at 42° C., to limit the cytotoxic effects of transposase. Six ampicilline resistance clones were put into culture under the same conditions to extract plasmides. The DNA mini-preparations were controlled by NcoI/HindIII digestion on 0.8% agarose gel (TAE 1×) to assure that they had integrated the gene coding for transposase.

1.2.4. Cloning the L27 Probe:

The sequence of the gene coding for the L27 ribosomal protein of E. Coli was obtained on the Infobiogen site (www.infobiogen.fr). The SEQ ID No. 6 and the SEQ ID No. 7 primers to amplify the gene by Polymerase Chain Reaction (PCR) were drawn using the OLIGOV2 software and then ordered in the form of single-strand oligonucleotides.

```
SEQ ID No. 6: 5'-ATGGCACATAAAAAGGCTG-3'

SEQ ID No. 7: 5'-TTATTCAGCTTCGATGCT-3'
```

The L27 gene was amplified using the PCR technique starting from the *E. coli* genomic DNA. Amplification products were eluted after electrophoresis on a 0.8% agarose gel and then ligatured in the pGEM®-T Easy vector before being cloned. Competent *E. Coli* bacteria (DH5α) were transformed with ligation mixes, and then spread on LB-ampicilline boxes (100 µg/ml) containing X-Gal (2%) and IPTG (1 mM). Two white ampicilline resistance clones were then put into culture to extract plasmidic DNA. After checking cloning by an EcoRI digestion and electrophoresis on an 0.8% agarose gel (TAE 1×), the plasmide was sequenced using the "DNA sequencing kit" (Perkin Elmer Biosystems) and analysed on a Licor type automatic monolaser sequencer to check that the sequence before marking had been conserved.

1.2.5. Marking of L27 and Tnp Probes

The L27 probe was marked by radioactive PCR from the pGEM-T (L27) matrix with pU and pRev primers (that surround the cloning site [Ausubel et al., 1994]) in the presence of ATP-$\gamma^{32}$P. The marked probe is separated from free dNTPs by size exclusion chromatography on a Sephadex G50 column (TE 1×: 10 mM tris pH 8, 1 mM EDTA). The column was washed by 200 µl fraction and the probe marked with the MIP counter 10 (Eurisys Mesures, Saint-Quentin-en-Yvelines, France).

The Tnp probe was marked using the "Random Priming" technique, in other words synthesis of DNA after matching of random hexamers. The elongation was made using the Klenow fragment of polymerase DNA in the presence of ATP-$\gamma^{32}$P. The probe was eluted by size exclusion chromatography on a Sephadex G50 column (TE 1×).

1.3. Induction of Bacteria Containing the Vector Coding for Transposase

| With pBadR-Tnp: | With pKK-Tnp: |
|---|---|
| 1% Glucose | Control (without IPTG) |
| Control (0% glc, 0% ara) | 0.5 mM IPTG |
| 0.001% arabinose | 1 mM IPTG |
| 0.01% arabinose | 3 mM IPTG |
| 0.1% arabinose | 6 mM IPTG |
| 1% arabinose | |

Induction Protocol:

Starting from a saturated culture of *E. coli* MC1061 bacteria containing the vector of interest (pBadR-Tnp or pKK-Tnp), 50 ml of LB was seeded to 1/100 and put into culture for 3 h at 31° C. while stirring (250 rpm) in the presence of 1% glucose (Para inhibitor) in the case of pBadR-Tnp. The culture was then centrifuged during 15 minutes at 3000 rpm and the residue was dissolved in 2.5 ml of LB in order to wash it and eliminate glucose. The same treatment was applied to the bacteria containing pKK-Tnp.

The induction tubes (2.5 ml LB containing arabinose or IPTG according to the conditions described above) were seeded volume by volume and put into culture for 3 h at 31° C. (final volume 5 ml). Proteins and mRNA were extracted after 3 hours. The same protocol was followed for bacteria containing pBadR and pKK plasmids, in order to produce RNA and proteins with no Tnp (negative controls).

1.4. Analysis of mRNAs 1.4.1. Extraction of Bacterial RNAs mRNAs were extracted at 4° C. in the absence of Rnase in order to prevent degradation.

After induction, the bacterial cultures were centrifuged for 10 minutes at 12 000 g, at 4° C. The supernatant was eliminated, the sediment dissolved in 5 ml of "protoplasting buffer" (15 mM Tris pH 8, 15% sucrose, 8 mM EDTA). 40 µl of lysosyme (50 mg/ml) was added and the mix was incubated for 15 minutes in ice. After 5 minutes centrifuging at 6000 g, at 4° C., and then elimination of the supernatant, the sediment was dissolved in 250 µl of lyse buffer (1.5% SDS, 1 mM sodium citrate, 10 mM NaCl, 10 mM Tris pH 8).

After transferring the lysate into 1.5 ml tubes, 7.5 µl of DEPC was added; the mixes were then incubated 5 minutes at 37° C. The tubes were cooled in ice and mixed by inversion with ½ volume of a saturated solution of NaCl. After incubation for 10 minutes in ice, the tubes were centrifuged for 10 minutes at 12 000 g. The supernatant was then transferred into 1.5 ml tubes and nucleic acids were precipitated with three volumes of cold 100% ethanol (EtOH). The tubes were put into place for 30 minutes at −80° C. or −20° C. for 16 h. The tubes were then centrifuged for 15 minutes at 12 000 g, at 4° C.

The supernatants were eliminated, sediments washed with 500 µl of 70% EtOH and then dried. The sediments (dissolved in 30 µl of H$_2$O DEPC) were submitted to the action of Dnasel for 1 h 30 at 37° C. After phenol-chloroform extraction and precipitation, the RNA sediments were washed and dried and then dissolved in 50 µl of H$_2$O DEPC. The extraction quality was checked with 5 µl of sample on 0.8% agarose gel (TAE 1×). The extracted RNAs were conserved at −80° C.

1.4.2. Analysis of RNAs

Total RNA quantities were analysed using a fluorescence spectrophotometer.

Each extract was diluted to the nearest 100 in 500 µl of water. Absorbance was measured at 260 nm (maximum absorption wavelength of nucleic acids) and at 280 nm (absorption wavelength of amino acids like tyrosine). If the ratio of 260 nM absorptions and 280 nM absorptions was between 1.8 and 2.1, the total quantity of mRNA extracted at a rate of 40 µg for an absorbance measurement at 260 nm in 1 ml could be quantified.

To quantify the transposase mRNAs, a constant quantity of total RNAs (calibrated using an RNA control, the RNA coding for the L27 ribosomal protein for which the quantity did not vary during the experiments) was deposited on a hybridising membrane. After thermal fixation (15 minutes at 80° C.), the membrane was pre-hybridised with the Church buffer (7% SDS, 1 mM EDTA, 0.5 M NaPO4 pH 7.2) so as to limit non-specific hybridising by saturation of the membrane for 1 h at 65° C.

Hybridising with the L27 Control Probe

The pre-hybridising buffer was replaced by the new "Church" buffer to which 6000 hits per minute (hpm) were added (using the MIP counter 10) of the probe marked L27. The membrane was hybridised overnight at 65° C. The membrane was then washed for 1 h with a 3×SSC buffer (20×SSC: 3M NaCl 0.3 M sodium citrate)/0.1% SDS then with an 1×SSC/0.1% SDS buffer. The presence of L27 mRNAs was detected and quantified with the Direct Imager (Packard, United states) in hpm. A constant quantity of L27 mRNA for each deposit should confirm the constant quantity of total RNA deposited. Otherwise, it should enable the correction of quantities of Tnp mRNA.

The membrane was then dehybridised by three rinsings with a 1% SDS solution brought to boiling point. The membrane was then once again pre-hybridised for lh at 65° C. before a new hybridisation.

Hybridisation with the Tnp Probe

The pre-hybridisation buffer was replaced by the new "Church" buffer to which 6000 hpm of the Tnp probe was added. The membrane was hybridised overnight at 65° C. The membrane was then rinsed for one hour with a 3×SSC/0.1% SDS buffer, then with an 1×SSC/0.1% SDS buffer. The presence of Tnp mRNA was detected with the Direct Imager: the quantity of Tnp mRNA present in deposits was expressed in hpm.

1.5. Analysis of Proteins 1.5.1. Extraction of Proteins

The induction protocol used for bacteria was the same as that used for mRNA extractions. Cultures were centrifuged for 10 minutes at 12 000 g at 4° C. Bacterial sediments were dissolved in 500 µl of a 20 mM Tris pH 9, 100 mM Nacl, 1 mM DTT buffer and was kept at −20° C. overnight. After sonication (1 30 s "pulse" at 25 W) and centrifuging at 10 000 g, 4° C. for 15 minutes, the proteic supernatants were sampled and then quantified by a Bradford analysis compared with a concentration of bovine serum albumen (BSA). After analysis, the proteic extracts were kept at −20° C.

1.5.2. Analysis of Proteins in SDS-PAGE:

Preparation of Samples and Electrophoresis:

A constant quantity (12 µg) of proteins was analysed. A volume of a load buffer was added to each extract, the assembly was denaturated at 100° C. for 5 minutes. The samples were deposited in an SDS-PAGE 10% acrylamide gel [375 mM Tris HCl pH 8.8, 0.1% SDS, 10% acrylamide (30:0.8)]. After electrophoresis for 16 h at 50 V, the gel was fixed in a 2% $H_3PO_4$-50% $CH_3OH$ solution under mild stirring for 2 h to 12 h.

Colouring of Gel with Colloidal Coomassie Blue:

The gel was washed in water three times for 30 minutes. This step was repeated with a 2% $H_3PO_4$ solution.

The gel was then placed in a 17% $CH_3OH$, 2% $H_3PO_4$ and 15% $(NH_4)_2SO_4$ solution for 1 hour. The gel was then coloured overnight in an identical fresh solution, to which 0.2% of colloidal Coomassie blue was added. The coloured gel was digitised with a scanner and was then dried.

1.5.3. Delay on Gel Analysis of the Extracted Transposases Activity:

This method was used to test the ITR 3' binding activity (ITR optimised for fixation of Tnp) of produced proteins. The ITR 3' was isolated from the pBS plasmide (3') by EcoRI/Xbal digestion, purified on a NuSieve 2% agarose gel (FMC products, United States), eluted and quantified. 100 ng of ITR 3' were marked with the Klenow fragment of polymerase DNA in the presence of dATP. After a phenol-chloroform extraction and precipitation, the sediment was dissolved in 40 µl of water to obtain ITR at a concentration of 50 nM.

5 µg or raw extracts was incubated with marked ITR 3' under the following conditions: 1 nM of probe, 1 µg of sonicated salmon sperm DNA, 5 mM of $MgCl_2$, 5% glycerol, 20 mM Tris pH9, for 15 minutes in ice. Each sample was deposited on a 9% hydrolink gel (Long Ranger, TEBU, Le Perray en Yvelines, France) (TBE 0.25×: 22.25 mM Tris, 22.25 mM boric acid, 2.5 mM dehydrated disodium EDTA). The delay was quantified with the Direct Imager (Packard) after electrophoresis and drying of the gel. A gel autoradiograph was then made.

1.6. Transposition Test

Induction Conditions

| With pBadR-Tnp: | With pKK-Tnp: |
|---|---|
| 1% Glucose | Control |
| Control | 0.5 mM IPTG |
| 0.001% arabinose | 1 mM IPTG |
| 0.01% arabinose | 3 mM IPTG |
| 0.1% arabinose | 6 mM IPTG |
| 1% arabinose | |

The principle of the transposition test is shown in FIG. 3.

Competent MC1061 bacteria were co-transformed with the pBC 3K3 plasmide (carrying a pseudo-mariner reporter of the transposition and the chloramphenicol resistance gene) and with the inducible vector coding for pBadR-Tnp or pKK-Tnp transposase (carrier of the ampicilline resistance gene) (FIG. 3A). Bacteria were selected on ampicilline and chloramphenicol to check the presence of two plasmides. A co-transformation was also done with the pBadR and pKK control plasmides.

The E. Coli MC1061 bacteria containing the pBC3K3 reporter vector and the vector coding for transposase, were put into a culture at 42° C. in 2.5 ml of LB-ampicilline (100 µg/ml) chloramphenicol (20 µg/ml)/50 mM $CaCl_2$ overnight (conditions limiting the activity of transposase). The culture was titrated on an LB box (10 µl of a solution enabling correct counting) and. on an LB-Kanamycine box (100 µg/ml) (50 µl of saturated culture). 2.5 ml of LB (containing arabinose or IPTG as mentioned above) were seeded at 1/100 and cultivated for 3 h at 31° C. (optimum transposase functioning temperature) and while stirring at 250 rpm (FIG. 3B). After 3 hours of induction, the culture was spread on an LB box (titration of bacteria) and an LB-kanamycine box (enumeration of transposition events) (FIG. 3C). The boxes were placed at 37° C. overnight. The next day, the colonies on the LB and LB-kanamycine boxes were counted, and the transposition frequency was then calculated as being equal to the total number of bacteria resistant to kanamycine in comparison with the total number of bacteria.

1.7. Binding at Equilibrium Saturation Experiments Scatchard Test

The principle of this test is to determine the affinity (Kd) of the transposase produced in a eukaryotic system for ITR 3' (ligand), using binding at equilibrium saturation experiments on delay on gel. The results are represented using the Scatchard method. For a constant quantity of proteic extracts, the quantity of ITR 3' marked in a concentration range surrounding the Kd is varied. After 15 minutes incubation in ice (under conditions identical to the experiments of delay on gel), the ITR-protein complexes were deposited on a 9% acrylamide native gel (Long Ranger, TEBU) (TBE 0.25×). After electrophoresis and drying, the gel was analysed with a Direct Imager (Packard). The quantity of ITR bonded to the protein and the total quantity of ITR were measured in hits per minute (hpm).

To Determine the Dissociation Coefficient (Kd):

The total quantity of ITR bonded to transposase (B) was subtracted from the total quantity of ITR present (T) to give the quantity of free ITR (F). The B/F ratio expressed as a function of the bonded ITR nM (B nM) resulted in a straight line with the slope of −1/Kd.

This test was done with a fusion protein, MBP-Tnp (given by Dr. S. Tourne) produced in insect cells using a baculovirus vector and with transposase produced in an in vitro eukaryote transcription/translation system (TnT® T7 Quick Coupled Transcription/Translation System, Promega) with the pTE-Tnp vector. This test was also carried out with Tnp and MBP-Tnp (derived from eukaryotic cells) that had been dephosphorylised for 30 minutes at 30° C. with calf intestinal phosphatase (CIP).

1.8 Phosphorylation Tests 1.8.1. Test in Prokaryotes:

25 ml of LB was seeded at 1/100 in the presence of inorganic phosphorus ($PiP^{33}$) for 3 h at 37° C., starting from a preliminary culture of BL21 bacteria containing the pET-Tnp vector. Synthesis of transposase was then induced in the presence of 1 mM of IPTG for 3 hours at 37° C. Proteins extracted from this culture were analysed on a 10% SDS-PAGE gel. After 16 hours electrophoresis. at 50 V, the gel was coloured with colloidal Coomassie blue. After drying, the gel was put in a cassette for autoradiography, in order to display phosphorylated proteins.

1.8.2. Test in Eukaryotes:

The pET-Tnp plasmide was used in an in vitro eukaryote transcription/translation system (rabbit) (TnT® T7 Quick coupled Transcription/Translation System, Promega) to enable synthesis of transposase identical to that previously produced in prokaryotes. This system enables phosphorylation of proteins. Phosphorylation of transposase, if any, should be displayed due to the addition of ATP-$\gamma^{32}$P during synthesis.

0.5 to 1 µg of pET-Tnp was incubated for 90 minutes at 30° C. with 40 µl of TnT mix in the presence of ATP-$\gamma^{32}$P. 5 µl of mix was denatured with the same volume of filler buffer, and then deposited in a 10% acrylamide SDS-PAGE gel. After electrophoresis, the gel was coloured with colloidal Coomassie blue and then dried. Autoradiographs were made of the gel to reveal the presence of the phosphorylated protein.

2. Results

The mariner Mos-1 transposon has a weak transposition activity in its natural host (D. mauritiana) compared with the P element (Rubin et al, 1982). A bacteria study model was developed so as to be able to analyse all steps in the transposition of the mariner Mos-1 in a simpler system than eukaryotic cells. This model revealed that transposition of a Mos-1 element carrying two type 3' ITRs was 10 000 times more efficient than the transposition of an element in a "natural" configuration, in other words carrying an ITR 5' and an ITR 3'.

This difference is observed in prokaryotes but not in eukaryotes, as is demonstrated by work carried out on *drosophila* by Dr. P Atkinson (University California Riverside) and on HeLa cells by Dr. S. Tourne (Tours University) (personal communications). The results obtained on eukaryotic cells in this context revealed a very weak transposition activity with the two mariner elements (3'/3' and 5'/3').

The steps limiting the activity of transposase in eukaryotes were identified in order to understand why the mariner Mos-1 transposase behaves differently in a prokaryotic system. Differences between prokaryote and eukaryotic transposases causing the reduction in the efficiency of the transposition when it occurs in a eukaryotic system were then determined. This was done by testing two early transposition steps: production of protein and binding to ITR. Finally, phosphorylation was tested, which is one possible regulation mode for Mos-1 transposase.

2.1. Inhibition of Transposition by Overproduction of Transposase

Lohe and Hartl (1996) have demonstrated that the transposition frequency in eukaryotes reduces when the mariner Mos-1 transposase is overexpressed. This phenomenon is called OPI for "Over Production Inhibition". The expression Over Production Inhibition (OPI) will be used in the following description.

In a first series of experiments, it was required to know if the transposase produced in a bacterial system was subjected to OPI.

This was done using two expression systems to analyse the transposition frequency variations of the mariner Mos-1 as a function of the quantity of transposase present in the bacteria. The pBadR-Tnp vector is a weak expression system in which transposase is under the control of a promoter inducible with arabinose (Para) and is modulable, in other words the quantity of protein produced depends on the quantity of inducer. pKK-Tnp is a strong expression system in which transposase is under the control of a promoter inducible with IPTG (Plac) and is not modulable.

2.1.1 Correlation Between the Induction Level/Quantity of mRNA/Quantity of Transposase:

It was checked that the quantities of Tnp mRNa and Tnp proteins were well correlated to induction conditions, in order to validate the expression vectors. pBadR-Tnp was cultivated in the absence of an inducer (check level) in the presence of glucose (Para repressor) and with a range of 0.001% to 1% of arabinose (Para inducer). pKK-Tnp was cultivated in the absence of an inducer (control level) and in the presence of a range of between 0.5 mM and 6 mM of IPTG (Plac inducer).

1) Characterisation of mRNAs

After induction and extraction, mRNAs were hybridised with a control probe L27 of ribosomic protein to calibrate quantities of RNA extracted under different culture conditions, and then with the transposase probe to quantify Tnp-RNA contents (FIGS. 4 and 6) in hpm. Detected Tnp mRNA quantities (converted to a percentage of the maximum detected quantity) are represented (Y axis) as a function of the different culture conditions (X axis) in FIGS. 5 and 7.

Analysis of the pBadR-Tnp Expression System:

Transposase mRNAs were absent in bacteria containing the pBadR control vector in the weak expression system (pBadR). However, they were present in bacteria containing the pBad-Tnp expression vector: the smallest quantities of Tnp mRNA were detected in the absence of arabinose or in the presence of glucose, and higher quantities were observed in all induction conditions with a maximum quantity of Tnp mRNA for 0.1% arabinose (FIGS. 4 and 5). These results indicated that the Para promoter was not completely repressed by glucose and that it included an expression leak in the absence of glucose/arabinose under the culture conditions described herein. The quantity of mRNA coding for the transposase followed the inducer range, except for the point with 1% arabinose. The correlation between the Tnp mRNA quantity and induction conditions in the pBadR system showed that this expression system was consistent with known operation of the promoter inducible with arabinose (Para). Only the induction point with 1% arabinose resulted in a reduction in the quantity of transposase mRNA. This difference could be explained by the strong concentration of arabinose used for the induction, which should saturate or even inhibit the induction system. Another phenomenon could also explain this result: repression of the system by a reduction in the number of pBadR-Tnp plasmide copies in the presence of a strong concentration of arabinose. The presence of Tnp mRNA in a glucose condition (Para repressor) showed that the promoter was not completely lockable, which had already been demonstrated by Guzman et al. (1995). Moreover, bacteria were cultivated in a rich medium (LB) for which the exact composition is not known (yeast and tryptone extracts), the medium possibly interacting with normal operation of the promoter, particularly with regard to the expression of the AraC gene coding for the Para repressor.

Analysis of the pKK-Tnp Expression System:

In the strong expression system (pKK), mRNAs coding for transposase were absent from bacteria containing the pKK control vector and present for bacteria containing the pKK-Tnp vector: weakly when there was no inducer, and strongly in the presence of IPTG. The maximum quantity was detected at 0.5 mM IPTG (FIG. 7). In a strong expression system (pKK-Tnp), the quantity of synthesized Tnp mRNA was once again consistent with known operation of the Plac promoter inducible with the IPTG. This promoter was not entirely repressed in the absence of an inducer, resulting in a synthesis of Tnp mRNA (FIGS. 6 and 7). On the other hand, the promoter was active in the presence of IPTG, resulting in a strong expression: the quantity of Tnp mRNA remained constant regardless of the concentration of IPTG.

2) Analysis of Proteins:

Proteins were obtained under the same conditions as RNAs. They were analysed in SDS-PAGE (FIG. 8A). The digital image of the gel was used to calculate the percentage of transposase in the different extracts using the Molecular Analyst software (Biorad, Ivry sur Seine, France). At the same time, the binding to ITR 3' activity of transposases obtained in the different extracts was tested by experiments of delay on gel (FIG. 8B). The graphs (FIGS. 9 and 10) show the percentage of transposase in the extracts (relative quantities) (y axis) as a function of the different induction conditions (x axis). The contents of Tnp mRNA were moved so as to correlate mRNA and protein.

Analysis of the pBadR-Tnp Expression System:

Proteins extracted from bacteria containing the pBadR control vector did not contain transposase as demonstrated by protein gel (FIG. 8A, track 1) and delay on gel analysis (FIG. 8B, track 1). The extracts obtained from bacteria containing the pBadR-Tnp vector (FIG. 8A, tracks 2 to 7) contained very low quantities of transposase in the absence of an inducer (2.42% of raw extract, track 3) or in the presence of glucose (1.04% of raw extract, track 2). Quantities obtained in the presence of an inducer were slightly higher (2.62% to 3.1% of raw extract, tracks 4 to 7). FIG. 5 shows that the quantity of transposase was well correlated to the quantity of Tnp mRNA, except for the higher induction point (1% arabinose) for which the quantity of protein increased while the quantity of mRNA reduced. This could be explained by the accumulation of transposases synthesized before the quantity of mRNA was regulated, at the beginning of induction. The delay on gel analysis (FIG. 8B) shows that there was no detectable delay, even for strong concentrations of raw extracts and for high quantities of inducer.

Therefore quantities of transposases produced with the pBadR-Tnp expression vector were very low, which agreed with the activity of the promoter inducible with arabinose, and could therefore explain the lack of a signal during experiments of delay on gel. Only the transposition test (biological test) could be used to validate or invalidate the activity of transposases produced with this system.

Analysis of the pKK-Tnp Expression System:

Proteins extracted from bacteria containing the pKK control vector did not contain transposase, as indicated by the protein gel (track 8 in FIG. 8A) and the delay on gel analysis (track 8 in FIG. 8B). The extracts obtained from bacteria containing the pKKTnp vector (FIG. 8A, tracks 9 to 13) contained small quantities of transposase in the absence of IPTG (2.37% of raw extract, track 9) and large quantities of transposase in the presence of IPTG (8.48% to 10.25% of raw extract, tracks 10 to 13). FIG. 7 shows the content of synthesized Tnp mRNA and transposase produced as a function of induction conditions: the quantity of Tnp produced varied in the same way as the quantity of mRNA, the minimum quantity being obtained in the absence of an inducer, the maximum regardless of the quantity of inducer. The binding to ITR activity was detected strongly in delay on gel when the quantity of transposase was high (tracks 10 to 13 in FIG. 8B).

The transposase of the mariner Mos-1 element produced in the pKK-Tnp system appeared to be always active regardless of the induction conditions (FIG. 8B). Therefore, large quantities of transposase did not appear to affect the binding to ITR 3' capacity.

These first results demonstrated a correlation between Tnp-RNA quantities produced and the quantity of transposases produced in the two expression systems.

2.1.2. Correlation Between Transposase Quantities/Transposition Frequencies:

The transposition test was carried out under the same conditions as were used to obtain proteins and mRNAs. The only difference was the additional presence of a transposition reporter vector (pBC 3K3) in the bacterial strains. This transposition test was used to determine if an increase in the quantity of transposase reduced the transposition frequency, as would be expected if the prokaryote transposase was subject to OPI.

Analysis of the pBadR-Tnp Expression System:

The analysis of transposase production demonstrated that protein was present in our cultures, even in the absence of an inducer (arabinose) or in the presence of a repressor (glucose). Transposition began even in the absence of induction (FIG. 9, glucose and control conditions). This confirmed that transposase has a strong activity, even in small quantities. For a minimum quantity of transposase (1.04% of raw extract in glucose condition), the transposition frequency was $26 \times 10^{-5}$. The transposition frequency of $68 \times 10^{-5}$ was maximum for transposase enrichment equal to 2.62% of the raw extract (induction point 0.001% of arabinose), which is a slight increase by a factor of 2.5. For induction points from 0.01% to 1% of arabinose, the transposition frequency remained at a constant value despite slight transposase enrichment compared with the 0.001% arabinose induction point.

Therefore transposition experiments in the pBadR-Tnp system indicated that the transposase was always active, even when produced in small quantities. Furthermore, the maximum transposition frequency was reached even at the first induction point (0.001% of arabinose) and then reached a plateau for the following induction points. Therefore Over-Production Inhibition (OPI) was not observed in the pBadR-Tnp system, which appeared normal, considering the small amount of transposase produced.

Analysis of the pKK-Tnp Expression System:

Analysis of the production of protein showed that transposase was produced regardless of the culture conditions (FIG. 7, tracks 9 to 13). FIG. 10 shows the transposition frequency as a function of induction conditions. Transposase enrichments were added in order to correlate these enrichments with transposition frequencies. The transposition frequency for a minimum quantity of transposase (in the lack of induction) was $8 \times 10^{-5}$. The maximum transposition frequency was $59 \times 10^{-5}$ for a transposase enrichment of 8.48% (corresponding to the first 0.5 mM IPTG induction point) and then reached a plateau for quantities of transposase with negligible variation (8 to 10% raw extracts for the following induction points). Therefore, these results indicated a saturation of the production system even at the first production point, which corresponded to functioning of the strong promoter inducible with IPTG. The OPI phenomenon was not observed in the pKK-Tnp system, despite the presence of high rates of transposase in raw extracts.

2.1.3. Conclusion on OPI

The quantity of transposase produced in the pBadR-Tnp expression system was low but was sufficient to have efficient transposition, even in the absence of an inducer. In the pKK-Tnp system, the transposase production represented up to 10% of bacterial protein and enabled detection of its activity by a biochemical test (delay on gel). But this higher production did not result in a higher transposition frequency compared with the pBadR. system. The transposition frequency was a maximum of ($59 \times 10^{-5}$) at the first induction point (0.5 mM IPTG), and comparable with that obtained using pBadR-Tnp ($68 \times 10^{-5}$) for the 0.001% arabinose induction point. This frequency was constant for other indication points. Unlike the eukaryotic system, all of these results appeared to show that no overproduction inhibition was detected in the prokaryotic system, which should result in a drop in the transposition frequency.

2.2. Affinity of Transposase for DNA

Therefore, there was a first behavioural difference between transposase of the mariner Mos-1 element produced in a eukaryotic and in a prokaryotic system: OPI only appeared to be involved in the eukaryotic system. The binding quality between the end 3' of the mariner Mos-1 transposon (ITR 3') and the transposase was tested in order to find other possible regulation levels of transposition. This is the first step involved during the transposition method. Saturation experiments on binding at equilibrium were carried out and analysed in delay on gel to determine the affinity of transposase for ITR (Kd measurement). FIGS. 1 and 12, insets). These experiments were carried out with a constant quantity of transposase in the presence of a ligand concentration range (therefore a concentration range of ITR 3'). The results obtained were shown according to Scatchard. In this type of representation, the ratio between the quantity of bonded ligand (ITR) and the quantity of free ligand (B/F) is expressed as a function of the concentration of bonded ligand (nM B) and is displayed by a straight line with equation $y=ax+b$, where $a=-1/Kd$.

These tests were already carried out on the transposase produced in a prokaryotic system, and were used to calculate a dissociation factor (Kd1) equal to 0.6 nM for binding to ITR 3' (publication submitted). A second Kd ($Kd_2=10$ nM) measured binding to ITR as an integration target. The same type of test was carried out with two mariner Mos-1 transposases produced in a eukaryotic system: MBP-Tnp fusion protein given by Dr. S. Tourne (Tnp coupled with a protein enabling purification but with no impact on its activity) produced in insect cells using a baculovirus system and extracted from the cell nucleus, and transposase produced in lysate of reticulocytes (rabbit) using the TnT® T7 Quick Coupled Transcription/Translation System kit (Promega).

The first experiment was carried out with MBP-Tnp under the same conditions as the experiments with bacterial origin transposase, in other words for a concentration range of ITR 3' between 0.05 nM and 10 nM. The results showed that these conditions were not adapted to determine a Kd (the ligand concentration range should "surround the Kd") and therefore that the eukaryotic protein behaved differently from the prokaryotic transposase.

Consequently, the range of ITR 3' was increased by moving between 2 nM and 50 nM. FIG. 11 shows the ratio of the bonded probe to the free probe (B/F) as a function of the concentration of bonded probes (nM B) which resulted in a single straight line with a slope equal to −0.0256. Kd was the inverse of the slope, and its value was 39 nM. Another Scatchard was carried out under the same conditions with the transposase produced from pET-Tnp using the TnT® system that can be used for in vitro transcription/translation in rabbit reticulocyte lysates. The result obtained (FIG. 12) showed a profile identical to that obtained with transposase produced in insect cells and with a single Kd of 74 nM.

This result indicated that the transposase produced in vitro in reticulocyte lysates had an affinity for binding to ITR 3' similar to a transposase produced in vivo in insect cells. Therefore, this in vitro synthesis kit was capable of producing a transposase with the same behaviour as a transposase produced in insect cells. With the two eukaryotic transposases, a real difference in affinity for the ITR 3' equal to a factor of about 100, was observed: the transposase produced in bacteria had a strong affinity for the ITR 3', while transposase produced in insect cells or in an in vitro eukaryotic system had a lower affinity.

2.3. Impact of Phosphorylation on the Transposase Activity

Differences in the behaviour of transposase were demonstrated depending on whether or not it was produced in prokaryotic cells or eukaryotic cells. Post-translational modifications that could have an impact on the behaviour of transposase were searched for in an attempt to determine the origin of these differences.

Starting from an assumption according to which transposase could potentially be affected by phosphorylations (among other post-translation modifications), the first step was to find whether or not the transposase was phosphorylated during its synthesis in eukaryotes and not phosphorylated in bacteria. Bacteria do not phosphorylate proteins with exogenous origin.

2.3.1. Phosphorylation of Transposase in Prokaryotes and/or Eukaryotes:

Bacteria containing the pET-Tnp vector were put into culture in the presence of an organic phosphorus ($pip^{33}$) so as to integrate it into the synthesized proteins.

The SDS-PAGE gel analysis coloured with colloidal Coomassie blue revealed the presence of a band corresponding to transposase for bacteria containing the pET-Tnp vector. Once the gel was dried, it was autoradiographed to check that there was no phosphorylation of the transposase in prokaryotes. The in vitro eukaryote transcriptions/translation kit was used in particular to study phosphorylation in the eukaryotic system, and to produce a transposase with an activity similar to that produced in vivo in insect cell. Production of transposase with pET-Tnp in reticulocyte lysate in the presence of ATP--$\gamma^{32}$ P, resulted in the appearance of radiomarked bands on the protein gel (FIG. 13, track 3), also present when the experiment was carried out in the absence of DNA (FIG. 13, track 1), or with pET-26b+(FIG. 13, track 2). A radiomarked band present only in the case of production with pET-Tnp (track 3 in FIG. 13) was located at a PM of about 40 kDa, similar to that of the transposase.

The results of these two experiments showed that transposase was not genuinely phosphorylated when it was produced in bacteria, while it was phosphorylated when it was produced in eukaryotic cells.

2.3.2. Impact of Phosphorylation on the Affinity of Transposase for DNA

The two proteins produced in the eukaryotic system were dephosphorylated so as to determine if phosphorylation was involved in the difference in activity between prokaryotic and eukaryotic transposases. A Scatchard test was then carried out with a wide ligand range (0.05 to 25 nM of ITR 3') so as to be sure that the Kd value(s) was (were) surrounded. FIGS. 14 and 15 have a profile similar to that obtained with the transposase produced in a prokaryotic system, in other words the presence of two straight lines and therefore two different Kd values. With the MBP-Tnp produced in insect cells and dephosphorylated (FIG. 14), the first Kd ($Kd_1$) was 0.66 nM and the second Kd ($Kd_2$) was 24.69 nM. These values were similar to the values obtained with "prokaryotic" transposase ($Kd_1$ equal to 0.6 nM and $Kd_2$ equal to 10 nM). For the "eukaryotic" transposase produced in vitro (FIG. 15), the value of $Kd_1$ was 1.3 nM and $Kd_2$ was 15.5 nM. Once again, these two values were in the same range as the values obtained with "prokaryotic" transposase.

2.4. Impact of a Mutation Making the Transposase Non-Phosphorylatable in at Least One Site, on the Transpositional Activity of this Transposase 2.4.1. Preliminary Results In accordance with the Results described in section 2.2 above, a bacterial origin transposase is about 100 times more efficient in recognizing ITRs and initiating transposition than a transposase with eukaryotic origin.

Therefore, post-translational phosphorylations affect the affinity of transposase for DNA (specific and non-specific) and limit the conformational activity of the transposase.

Therefore specific binding of each transposase monomer to each of the two transposon ITRs is reduced by a factor of about 100, the reduction of efficiency in the transposition provoked by phosphorylation, at least at the T88 position, is evaluated as being a factor equal to about the square of 100.

The mutation of the theoretical residue in position 88 into a non-phosphorylatable alanine residue, using a conventional isolated mutagenesis method (Ausubel et al., 1994) appears to increase the aptitude of the transposase thus mutated to catalyse the transposition and transfer of DNA by a factor of between about 100 and 1000 compared with the value for a native transposase.

2.4.2. Impact of a Mutation Making the Transposase Non-Phosphorylatable in at Least One Site, on the Transpositional Activity: Importance of a Conservative Substitution As shown in FIG. 16 (A and B), the results of analyses carried out on mutant transposases described in Zhang et al. (2001) show that the S104P transposase is not capable of binding to ITRs and mediating transposition in bacteria. For the S302P transposase, the results show that this transposase is not capable of forming all binding complexes to ITR. Furthermore, it is incapable of mediating the transposition.

The same analyses were carried out in a reasoned manner on mutated transposases on the T88 position (FIG. 16, C and D).

This position was chosen because it has been demonstrated that the T88 and S99 and S104 positions are phosphorylated in eukaryotes, using antibodies in contact with phosphorylated serines (Qiagen), phosphorylated threonines (Qiagen) and SQ and TQ dipeptides phosphorylated on serine or threonine (New England Biolabs).

The results of impact analysis of the various mutations in the T88 position show that only the T88V transposase is capable of maintaining an aptitude to mediate the transposition that is not significantly different from the mediation of native transposase. They also show that mutations such as mutation of T88E and T88R transposases very much reduce the formation of larger complexes and completely inhibit the capability of mediating the transposition. Finally, these experiments reveal that for amino acids closest to threonine (A, C and V), the only genuinely conservative substitution is a substitution by valine.

REFERENCES

Augé-Gouillou C et al. (2001) Mol. Genet. Genomics. 265: 51-57

Lampe D J et al. (1996) EMBO J. 15: 5470-5479

Plasterk R H A et al. (1999) Trends in genetics 15: 326-332

Renault S. et al. (1997) Virology 1: 133-144

Jacobson and Hartl (1995) Genetics 111: 57-65

Craig et al. (2002) Mobile DNA II. ASM Press, Washington. USA Sambrook and Russel (2001) Molecular Cloning: a laboratory manual ($3^{rd}$ Ed.) Cold Spring Harbor Laboratory Press. Cold Spring Harbor, N.Y.

Guzman et al. (1995) J. Bacteriol 177: 4121-4130

Lohe et Hartl (1996) Mol. Biol. Evol. 13: 549-555

Rubin and Spradling (1982) Science 218: 348-353

Jeong et al. (2002) PNAS 99: 1076-1081

Martienssen and colot (2001) Science 293: 1070-1074

Ketting et al. (1999) Cell 99: 133-141

Tabara et al. (1999) cell 99: 123-132

Zhang et al. (2001) Nucl. Acids Res. 29: 3566-3575

Felsenstein (1993) PHILIPS (Phylogeny Inference Package) version 3.5.c, University of Washington, Seattle Augé-Gouillou et al. (2000) Mol. Gen. Genet. 264: 514-520

Ausubel et al. (1994) In Janssen, K. (Ed) Current Protocols in Molecular Biology. J. Wiley & Sons, INC Massachusetts General Hospital, Harvard Medical School.

Mornon et al. (2002) Cell. Mol. Life Sci. 59: 2144-2154

Kastan et al. (2000) Nat. Rev. Mol. Cell. Biol. 1: 179-186 (Review)

Kastan et al. (2001) Acta Oncol. 40: 686-688 (Review)

The invention claimed is:

1. A purified mutant hyperactive transposase of a mariner mobile genetic element (MGE), having at least one mutation by conservative substitution of at least one phosphorylatable residue in at least one phosphorylation site, said conservative substitution making said phosphorylation site non-phosphorylatable in vivo, said phosphorylatable residue being selected from the group consisting of:

the following residues in sequence SEQ ID NO: 2: T11; T24; S28; T88; S99; S104; T135; S147; T154; S170; T181; S200; T216; T255; and S305, and corresponding residues in the sequence of a mariner MGE transposase aligned with said sequence SEQ ID NO: 2, said corresponding residues being selected from the group consisting of:
a serine; and
a threonine,
wherein said conservative substitution does not comprise substituting said phosphorylatable residue with a residue selected from the group consisting of serine, threonine, aspartic acid, glutamic acid, and proline.

2. The purified mutant transposase according to claim 1, having at least one mutation by conservative substitution of at least one phosphorylatable residue in each phosphorylation site, said conservative substitution making each site non-phosphorylatable in vivo.

3. The purified mutant transposase according to claim 1, wherein said phosphorylatable residue is substituted by a non-phosphorylatable residue.

4. The purified mutant transposase according to claim 1, which is hyperactive for at least one function selected from the group consisting of specific and non-specific DNA binding, dimerisation, transfer of DNA strands, and endonucleasic and nuclear internalization properties.

5. The purified mutant transposase according to claim 1, wherein said mariner genetic mobile element belongs to the mauritiana subfamily.

6. The purified mutant transposase according to claim 1, wherein said mariner genetic mobile element is mos-1.

7. The purified mutant transposase according to claim 6, wherein said phosphorylatable residue is selected from the group consisting of the following residues of SEQ ID NO: 2: T11; T24; S28; T88; S99; S104; T135; S147; T154; S170; T181; S200; T216; T255; and S305.

8. The purified mutant transposase according to claim 7, wherein said phosphorylatable residue is T88.

9. The purified mutant transposase according to claim 7, wherein said phosphorylatable residue is S104.

10. An isolated polynucleotide coding for a transposase according to claim 1.

11. A vector comprising the isolated polynucleotide according to claim 10.

12. A vector according to claim 11, which expresses said polynucleotide.

13. A recombinant host cell which harbors the vector according to claim 11.

14. A method for producing a mutant transposase comprising:
a) cloning the polynucleotide of claim 10 into an expression vector;
b) transforming a host cell with said expression vector; and
c) expressing said polynucleotide by said host cell.

15. The method according to claim 14, further comprising a prior step for obtaining said isolated polynucleotide by substituting at least one nucleotide of a triplet coding for a phosphorylatable residue by another nucleotide, in the nucleotidic sequence coding for the corresponding native transposase, so that the resulting triplet codes for a non-phosphorylatable residue.

16. The method according to claim 14, further comprising a subsequent step of purifying said mutant transposase.

17. A method of in vitro transposition of a transposable DNA sequence of interest to a target DNA sequence comprising using a mutant transposase according to claim 1.

18. A method of preparing a medicament for in vivo transposition of a sequence of transposable DNA of interest into the host genome comprising using a mutant transposase according to claim 1.

19. A method of in vivo transposition of a sequence of transposable DNA of interest into the host genome comprising using a mutant transposase according to claim 1.

* * * * *

SEQUENCE LISTING

<160> NUMBER OF SEQ ID NOS: 7

<210> SEQ ID NO 1
<211> LENGTH: 1286
<212> TYPE: DNA
<213> ORGANISM: Drosohila Mauritiana
<220> FEATURE:
<221> NAME/KEY: CDS
<222> LOCATION: (172)..(1206)

<400> SEQUENCE: 1

```
ccaggtgtac aagtagggaa tgtcggttcg aacatataga tgtctcgcaa acgtaaatat       60
ttatcgattg tcataaaact ttgaccttgt gaagtgtcaa ccttgactgt cgaaccacca      120
tagtttggcg caaattgagc gtcataattg tttactctca gtgcagtcaa c atg tcg      177
                                                          Met Ser
                                                            1 agt ttc gtg ccg aat aaa gag caa acg cgg aca gta tta att ttc tgt       225
Ser Phe Val Pro Asn Lys Glu Gln Thr Arg Thr Val Leu Ile Phe Cys
        5                  10                  15 ttt cat ttg aag aaa aca gct gcg gaa tcg cac cga atg ctt gtt gaa       273
Phe His Leu Lys Lys Thr Ala Ala Glu Ser His Arg Met Leu Val Glu
 20                  25                  30 gcc ttt ggc gaa caa gta cca act gtg aaa acg tgt gaa cgg tgg ttt       321
Ala Phe Gly Glu Gln Val Pro Thr Val Lys Thr Cys Glu Arg Trp Phe
 35                  40                  45                  50 caa cgc ttc aaa agt ggt gat ttt gac gtc gac gac aaa gag cac gga       369
Gln Arg Phe Lys Ser Gly Asp Phe Asp Val Asp Asp Lys Glu His Gly
                 55                  60                  65 aaa ccg cca aaa agg tac gaa gac gcc gaa ctg caa gca tta ttg gat       417
Lys Pro Pro Lys Arg Tyr Glu Asp Ala Glu Leu Gln Ala Leu Leu Asp
             70                  75                  80 gaa gac gat gct caa acg caa aaa caa ctc gca gag cag ttg gaa gta       465
Glu Asp Asp Ala Gln Thr Gln Lys Gln Leu Ala Glu Gln Leu Glu Val
         85                  90                  95 agt caa caa gca gtt tcc aat cgc ttg cga gag atg gga aag att cag       513
Ser Gln Gln Ala Val Ser Asn Arg Leu Arg Glu Met Gly Lys Ile Gln
    100                 105                 110 aag gtc ggt aga tgg gtg cca cat gag ttg aac gag agg cag atg gag       561
Lys Val Gly Arg Trp Val Pro His Glu Leu Asn Glu Arg Gln Met Glu
115                 120                 125                 130 agg cgc aaa aac aca tgc gaa att ttg ctt tca cga tac aaa agg aag       609
Arg Arg Lys Asn Thr Cys Glu Ile Leu Leu Ser Arg Tyr Lys Arg Lys
                135                 140                 145 tcg ttt ttg cat cgt atc gtt act ggc gat gaa aaa tgg atc ttt ttt       657
Ser Phe Leu His Arg Ile Val Thr Gly Asp Glu Lys Trp Ile Phe Phe
            150                 155                 160 gtt aat cct aaa cgt aaa aag tca tac gtt gat cct gga caa ccg tcc       705
Val Asn Pro Lys Arg Lys Lys Ser Tyr Val Asp Pro Gly Gln Pro Ser
        165                 170                 175 aca tcg act gct cga ccg aat cgc ttt ggc aag aag acg atg ctc tgt       753
Thr Ser Thr Ala Arg Pro Asn Arg Phe Gly Lys Lys Thr Met Leu Cys
    180                 185                 190 gtt tgg tgg gat cag agc ggt gtc att tac tat gag ctc ttg aaa ccc       801
Val Trp Trp Asp Gln Ser Gly Val Ile Tyr Tyr Glu Leu Leu Lys Pro
195                 200                 205                 210 ggc gaa acg gtg aat acg gca cgc tac caa caa caa ttg atc aat ttg       849
Gly Glu Thr Val Asn Thr Ala Arg Tyr Gln Gln Gln Leu Ile Asn Leu
                215                 220                 225
```

| | | | | | | | | | | | | | | | | |
|---|---|---|---|---|---|---|---|---|---|---|---|---|---|---|---|---|
| aac | cgt | gcg | ctt | cag | aga | aaa | cga | ccg | gaa | tat | caa | aaa | aga | caa | cac | 897 |
| Asn | Arg | Ala | Leu | Gln | Arg | Lys | Arg | Pro | Glu | Tyr | Gln | Lys | Arg | Gln | His | |
| | | | 230 | | | | | 235 | | | | | 240 | | | |
| agg | gtc | att | ttt | ctc | cat | gac | aac | gct | cca | tca | cat | acg | gca | aga | gcg | 945 |
| Arg | Val | Ile | Phe | Leu | His | Asp | Asn | Ala | Pro | Ser | His | Thr | Ala | Arg | Ala | |
| | | 245 | | | | | 250 | | | | | 255 | | | | |
| gtt | cgc | gac | acg | ttg | gaa | aca | ctc | aat | tgg | gaa | gtg | ctt | ccg | cat | gcg | 993 |
| Val | Arg | Asp | Thr | Leu | Glu | Thr | Leu | Asn | Trp | Glu | Val | Leu | Pro | His | Ala | |
| | 260 | | | | | 265 | | | | | 270 | | | | | |
| gct | tac | tca | cca | gac | ctg | gcc | cca | tcc | gat | tac | cac | cta | ttc | gct | tcg | 1041 |
| Ala | Tyr | Ser | Pro | Asp | Leu | Ala | Pro | Ser | Asp | Tyr | His | Leu | Phe | Ala | Ser | |
| 275 | | | | | 280 | | | | | 285 | | | | | 290 | |
| atg | gga | cac | gca | ctc | gct | gag | cag | cgc | ttc | gat | tct | tac | gaa | agt | gtg | 1089 |
| Met | Gly | His | Ala | Leu | Ala | Glu | Gln | Arg | Phe | Asp | Ser | Tyr | Glu | Ser | Val | |
| | | | | 295 | | | | | 300 | | | | | 305 | | |
| aaa | aaa | tgg | ctc | gat | gaa | tgg | ttc | gcc | gca | aaa | gac | gat | gag | ttc | tac | 1137 |
| Lys | Lys | Trp | Leu | Asp | Glu | Trp | Phe | Ala | Ala | Lys | Asp | Asp | Glu | Phe | Tyr | |
| | | | 310 | | | | | 315 | | | | | 320 | | | |
| tgg | cgt | gga | atc | cac | aaa | ttg | ccc | gag | aga | tgg | gaa | aaa | tgt | gta | gct | 1185 |
| Trp | Arg | Gly | Ile | His | Lys | Leu | Pro | Glu | Arg | Trp | Glu | Lys | Cys | Val | Ala | |
| | | 325 | | | | | 330 | | | | | 335 | | | | |
| agc | gac | ggc | aaa | tac | ttt | gaa | taaatgattt | | tttcttttc | | cacaaaattt | | | | | 1236 |
| Ser | Asp | Gly | Lys | Tyr | Phe | Glu | | | | | | | | | | |
| | 340 | | | | | 345 | | | | | | | | | | | aacgtgtttt ttgatttaaa aaaaacgaca tttcatactt gtacacctga 1286

<210> SEQ ID NO 2
<211> LENGTH: 345
<212> TYPE: PRT
<213> ORGANISM: Drosohila Mauritiana

<400> SEQUENCE: 2

Met Ser Ser Phe Val Pro Asn Lys Glu Gln Thr Arg Thr Val Leu Ile
1               5                   10                  15

Phe Cys Phe His Leu Lys Lys Thr Ala Ala Glu Ser His Arg Met Leu
                20                  25                  30

Val Glu Ala Phe Gly Glu Gln Val Pro Thr Val Lys Thr Cys Glu Arg
            35                  40                  45

Trp Phe Gln Arg Phe Lys Ser Gly Asp Phe Asp Val Asp Asp Lys Glu
        50                  55                  60

His Gly Lys Pro Pro Lys Arg Tyr Glu Asp Ala Glu Leu Gln Ala Leu
65                  70                  75                  80

Leu Asp Glu Asp Asp Ala Gln Thr Gln Lys Gln Leu Ala Glu Gln Leu
                85                  90                  95

Glu Val Ser Gln Gln Ala Val Ser Asn Arg Leu Arg Glu Met Gly Lys
            100                 105                 110

Ile Gln Lys Val Gly Arg Trp Val Pro His Glu Leu Asn Glu Arg Gln
        115                 120                 125

Met Glu Arg Arg Lys Asn Thr Cys Glu Ile Leu Leu Ser Arg Tyr Lys
130                 135                 140

Arg Lys Ser Phe Leu His Arg Ile Val Thr Gly Asp Glu Lys Trp Ile
145                 150                 155                 160

Phe Phe Val Asn Pro Lys Arg Lys Ser Tyr Val Asp Pro Gly Gln
                165                 170                 175

Pro Ser Thr Ser Thr Ala Arg Pro Asn Arg Phe Gly Lys Lys Thr Met
            180                 185                 190

Leu Cys Val Trp Trp Asp Gln Ser Gly Val Ile Tyr Tyr Glu Leu Leu

```
            195                 200                 205
Lys Pro Gly Glu Thr Val Asn Thr Ala Arg Tyr Gln Gln Gln Leu Ile
    210                 215                 220

Asn Leu Asn Arg Ala Leu Gln Arg Lys Arg Pro Glu Tyr Gln Lys Arg
225                 230                 235                 240

Gln His Arg Val Ile Phe Leu His Asp Asn Ala Pro Ser His Thr Ala
                245                 250                 255

Arg Ala Val Arg Asp Thr Leu Glu Thr Leu Asn Trp Glu Val Leu Pro
            260                 265                 270

His Ala Ala Tyr Ser Pro Asp Leu Ala Pro Ser Asp Tyr His Leu Phe
        275                 280                 285

Ala Ser Met Gly His Ala Leu Ala Glu Gln Arg Phe Asp Ser Tyr Glu
    290                 295                 300

Ser Val Lys Lys Trp Leu Asp Glu Trp Phe Ala Ala Lys Asp Asp Glu
305                 310                 315                 320

Phe Tyr Trp Arg Gly Ile His Lys Leu Pro Glu Arg Trp Glu Lys Cys
                325                 330                 335

Val Ala Ser Asp Gly Lys Tyr Phe Glu
            340                 345

<210> SEQ ID NO 3
<211> LENGTH: 19
<212> TYPE: DNA
<213> ORGANISM: Artificial Sequence
<220> FEATURE:
<223> OTHER INFORMATION: Primer - Translation initiating consensus
      site - pBad18 vector

<400> SEQUENCE: 3
gaaggagtac ccgggatc                                                    19

<210> SEQ ID NO 4
<211> LENGTH: 21
<212> TYPE: DNA
<213> ORGANISM: Artificial sequence
<220> FEATURE:
<223> OTHER INFORMATION: Primer - pBadR-Tnp construct

<400> SEQUENCE: 4
aattcgatat cgaaggagta c                                                21

<210> SEQ ID NO 5
<211> LENGTH: 13
<212> TYPE: DNA
<213> ORGANISM: Artificial sequence
<220> FEATURE:
<223> OTHER INFORMATION: Primer - pBadR-Tnp construct

<400> SEQUENCE: 5
gctatagctt cct                                                         13

<210> SEQ ID NO 6
<211> LENGTH: 19
<212> TYPE: DNA
<213> ORGANISM: Artificial sequence
<220> FEATURE:
<223> OTHER INFORMATION: PCR Primer

<400> SEQUENCE: 6
atggcacata aaaaggctg                                                   19
```

-continued

```
<210> SEQ ID NO 7
<211> LENGTH: 18
<212> TYPE: DNA
<213> ORGANISM: Artificial sequence
<220> FEATURE:
<223> OTHER INFORMATION: PCR primer

<400> SEQUENCE: 7
ttattcagct tcgatgct                                                   18
```